United States Patent [19]
Børretzen et al.

[11] Patent Number: 6,153,594
[45] Date of Patent: Nov. 28, 2000

[54] 5'-O-ACYLATED ANTIVIRAL NUCLEOSIDES

[75] Inventors: Bernt Børretzen, Heistad; Are Dalen, Trondheim; Finn Myhren, Porsgrunn; Kjell Torgeir Stokke, Oslo, all of Norway

[73] Assignee: Norsk Hydro as, Oslo, Norway

[21] Appl. No.: 08/532,754

[22] PCT Filed: Apr. 5, 1994

[86] PCT No.: PCT/NO94/00071

§ 371 Date: Nov. 29, 1995

§ 102(e) Date: Nov. 29, 1995

[87] PCT Pub. No.: WO94/22887

PCT Pub. Date: Oct. 13, 1994

[30] Foreign Application Priority Data

Apr. 5, 1993 [GB] United Kingdom .................. 9307043

[51] Int. Cl.⁷ .......................... A61K 31/70; C07H 19/02; C07H 19/06; C07H 19/16
[52] U.S. Cl. .................... 514/43; 514/45; 514/46; 514/49; 514/50; 514/261; 514/262; 514/269; 536/27.6; 536/27.81; 536/28.54; 544/276; 544/277; 534/767
[58] Field of Search .................. 514/43, 45, 49, 514/50, 46, 261, 262, 269; 536/27.6, 27.81, 28.54; 544/276, 277; 534/767

[56] References Cited

U.S. PATENT DOCUMENTS

| | | | |
|---|---|---|---|
| 3,920,630 | 11/1975 | Wechter et al. | 260/211.5 R |
| 3,960,836 | 6/1976 | Gutowski | 514/42 |
| 3,984,396 | 10/1976 | Witkowski et al. | |
| 3,998,807 | 12/1976 | Moffatt | |
| 4,097,665 | 6/1978 | Ishida et al. | |
| 4,531,001 | 7/1985 | Robins et al. | 536/55 |
| 4,740,503 | 4/1988 | Hori et al. | 514/51 |
| 5,216,142 | 6/1993 | Horrobin et al. | 514/50 |
| 5,405,837 | 4/1995 | Weber | 514/43 |

FOREIGN PATENT DOCUMENTS

| | | |
|---|---|---|
| 0 056 265 A2 | 7/1982 | European Pat. Off. |
| 0 393 920 A2 | 10/1990 | European Pat. Off. |
| 2 511 828 | 10/1975 | Germany . |
| 57-62294 | 4/1982 | Japan . |
| 61-171498 | 8/1986 | Japan . |
| 64-83092 | 3/1989 | Japan . |
| 2-78696 | 3/1990 | Japan . |
| WO 90/555 | 1/1990 | WIPO . |
| WO 93/7163 | 4/1993 | WIPO . |

OTHER PUBLICATIONS

Hamamura, et al., "Reactions of 2–Acyloxyisobutyl Halides with Nucleosides . . . ", J. Med. Chem., vol. 19, No. 5, pp. 667–674 (1976).

Rubas, et al., "Treatment of Murine L1210 Lymphoid Leukemia . . . ", Int. J. Cancer: 37, pp. 149–154 (1986).

Ozaki, et al., "5–Fluorouracil Derivatives", Chemical and Pharmaceutical Bulletin, vol. 38, No. 11, pp. 3164–3166 (1990).

*Primary Examiner*—Gary L. Kunz
*Attorney, Agent, or Firm*—Fitzpatrick, Cella, Harper & Scinto

[57] ABSTRACT

A monoester compound of formula I:

Nu—O—Fa wherein O is oxygen, Nu is a nucleoside analog, Fa is an acyl group of a mono-unsaturated C18 or C20 omega-9 fatty acid, which fatty acid is esterified with a hydroxyl group in the 5'-position of the sugar moiety of the nucleoside analog or with a terminal hydroxyl group on the non-cyclic group of the nucleoside analog, and wherein Nu is represented by the formula II:

B—S wherein S is a mono-saccharide derivative and B is a heterocyclic ring system.

9 Claims, 17 Drawing Sheets

2'-Deoxy-coformycin Oleate

2'-Deoxy-coformycin Elaidate

2'-Deoxy-coformycin Eicosenate, cis

2'-Deoxy-coformycin Eicosenate, trans

BV-ARA-U Oleate

BV-ARA-U Elaidate

BV-ARA-U Eicosenate, cis

BV-ARA-U Eicosenate, trans

FIG. 4J

2'-F-ARA-Ribavirin Oleate

2'-F-ARA-Ribavirin Elaidate

2'-F-ARA-Ribavirin Eicosenate, cis

2'-F-ARA-Ribavirin Eicosenate, trans

FIG. 4N

5'-O-ACYLATED ANTIVIRAL NUCLEOSIDES

This application is a 371 of PCT/NO94/00071 filed Apr. 5, 1994.

Present invention relates to a group of new compounds of the general formula I:

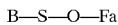

wherein B—S constitutes a nucleoside analogue in which B represents an optionally substituted heterocyclic ring system, S being a monosaccharide derivative, O representing an oxygen, and Fa is an acyl group of a monounsaturated C18 or 20 fatty acid. The invention also concerns anti viral pharmaceutical and veterinary compositions comprising a compound of formula I alone or in combination with a pharmaceutically acceptable carrier. A further part of this invention is a method for the treatment of a human or animal patient suffering from a viral infection and for reducing the infectious load by administering a compound of formula I. Likewise, certain compounds of formula I can be used as an antibiotic or in the treatment of a cancerous disease.

TECHNICAL BACKGROUND

A large number of serious diseases, such as AIDS, hepatitis B, herpes and gynecological cancer, as a late result of papilloma warts, are caused by viral infections.

Viruses are small infectious agents which are incapable of independent replication and thus are dependent on a host cell to replicate. The genetic material of the virus is either RNA or DNA.

When infecting an organism, the virus attaches to a specific host cell. The virus penetrates the cytoplasmic membrane after attachment and the viral genome is released from the virus particle. The viral genome is usually transported to the cell nucleus where new viral genomes are replicated. New viral protein is synthesized in the cytoplasm and new particles are formed either close to the cytoplasmic or nuclear membrane.

Some virus have genomic material which is directly (DNA viruses) or indirectly (Reverse transcription of RNA, retrovirus) incorporated in the host cell genomes.

Extracellular viruses are neutralized by circulating antibodies and the cellular immune apparatus may attack and remove infected cells. Viruses within the infected cells escape immune surveillance if viral antigens are not exposed on the surface of the cells.

The immune attack on infected organs contributes to disease by a mechanism commonly called virus induced immunopathology.

The mechanisms underlying some of the more important viral diseases differ.

When suffering from an HIV infection, the patient's T helper cells are invaded and destroyed. This leads to an immunodeficiency condition, which makes the patient very susceptible even to infections which normally are conquered by the immune system without any harmful effects for the patient.

The Hepatitis B virus invades the liver cells, and the patient may become very ill when the immune system tries to rid the body of these infected cells. If the infection is not conquered by the immune system at an early stage, the result will be chronic hepatitis. The patient will thus be infectious throughout his life. For a group of patients the chronic hepatitis will develop into cirrhosis or cancer of the liver.

In herpes simplex infections, the virus enters the epidermal cells originally. The herpes simplex virus travels up to a nerve center where it lies latent to break out at intervals. Although not life threatening in most cases, a herpes infection is painful and the patient will be infectious every time an outbreak occurs.

In the papilloma virus, notably in the genital tract of women, the viral genome is located in the nucleus of epithelial cells, but not integrated in the cell chromosomes. This is a persistent condition and with some tumor promoting strains an integration finally occurs which leads to a malignant development. The viral genome in this case has a decisive initiating effect in the process leading to cancer.

If the immune system manages to rid the body of the virus at an early stage, this leads to a life-long immunity. On the other hand, if the virus is too aggressive and avoids the immune apparatus, no immunity is achieved and a continuous infectious state is the result.

As a result of the different mechanisms, the therapeutic strategy would be different for these conditions.

The ultimate goal in the treatment of HIV/AIDS would be to free the patient from the infectious virus. This seems to be remote at the present stage, However, much can be obtained by improving the general condition of the patient. A reduction of the virus load would increase the length of the symptom free period and reduce the infectiousness, which is of utmost importance in regard to the epidemiological situation. All currently used anti-viral agents have toxic side effects, which presently makes a sufficiently aggressive treatment impossible.

It is assumed that there are between 250 and 300 million carriers of hepatitis B worldwide. It is known that a great number of these are going to develop hepatomas or liver insufficiencies due to the infections. Promising results in the treatment of the carrier state have been obtained in recent years by induction of an immune response with interferon. Therapies reducing the virus load is important in this regimen as efficient treatment of acute hepatits B would reduce the number developing into a carrier state. The recently identified hepatitis C virus causes a very great number of cases with hepatitis whereof a large number develop into carriers. Preliminary studies seem to indicate that the carrier state may be broken by similar therapeutic regimens as for hepatitis B.

Herpes simplex 1 and 2 frequently infect humans causing a carrier state with recurrencies of local infections. Generalized infections including encephalitis are rare but a catastrophy for the patient. There is a great individual variation in the frequency of local infections. For those patients who are affected either genitally or facially this constitutes a serious health problem physically, mentally and socially. None of the therapeutic regimens developed so far cures the latent infections of cells in the central nervous system. The therapeutic goal is thus to minimize the clinical manifestations of recurrencies both as to symptoms and duration.

The prevalence of genital papilloma virus infections has increased dramatically during the 1980s. It is now established that some genotypes are oncogenic, that is, they initiate changes in the cell which after a latency period develop into cancer. Papilloma virus of the genital tract gives long standing infections. The factors causing malignant transformation of the lesions are not well understood, but the immune system is assumed to be of importance. It is thought that the lesions showing progression during the months and years are those giving rise to cancer. The genital papillomas called condylomas are at present treated by physical means such as surgical removal, necrotizing means, fluid nitrogen or the like. Genital warts are at the onset benign tumors with altered enzyme patterns affecting among other things the metabolism of nucleoside analogues. Nucleoside prodrugs affect the episomal proliferation of papilloma virus thereby inducing regression of the warts.

Prophylactic vaccination has been very successful in acute infections such as polio, measles, mumps etc, but no effective vaccination has been developed for many of the other serious viral infections.

Even though there have been intensive efforts to produce effective anti-viral chemotherapeutica during the last decades, no satisfactory medical treatment can be offered for most viral diseases today. The efforts have been especially great since the appearance of the HIV and related viral infections, which are spreading throughout the world at an alarming rate, yet the effects obtained with agents such as azidothymidin (AZT) and acyclovir (ACV) in AIDS and herpes can only be characterized as partially successful. These most promising anti-viral agents are thus derivatives of naturally occurring nucleosides, which have been modified either in the base or sugar moiety. They have, however, not had the therapeutic potential hoped for, as they bring forward serious side-effects in some patients or show little or no effect in others. Further, treatment with these agents is extremely expensive. For these reasons only patients suffering from the very serious viral infections such as AIDS receive such treatment. Patients suffering from the less serious, but also very painful viral infections are often left without any treatment and the infection is allowed to take its own course.

The untreated patient carries a great infectious load and constitutes a risk to his fellow human beings. If he is treated with an anti-viral agent, the aim is to reduce the infectious load so as to enable the body's immune system to conquer the infection. A further aim is to reduce the contagiousness and thus the number of new patients and carriers.

Thus the need for compounds having a better therapeutic index is obvious.

The need is especially great in chronic or recurrent viral infections with a dangerous acute phase or long term ill effects on health or well being, such as AIDS, hepatitis B and C, infections of the herpes group and papilloma viral infections. Similarily, there is also a need for anti-viral agents usable in the treatment of animals suffering from viral diseases.

PRIOR ART

In order to improve their effectiveness, there have been developed derivatives of the nuclosides have been developed that are either modified in the in particular fatty acid esters of the nucleoside analogues have been developed in order to improve the lipophilicity and achieve a better membrane passage.

Thus there are known from U.S. Pat. No. 3,984,396 (Witkowski et al) esters of ribavirin with aromatic and saturated fatty acids having 1–18 C-atoms.

DEFINITION OF THE INVENTION

Figure 1:
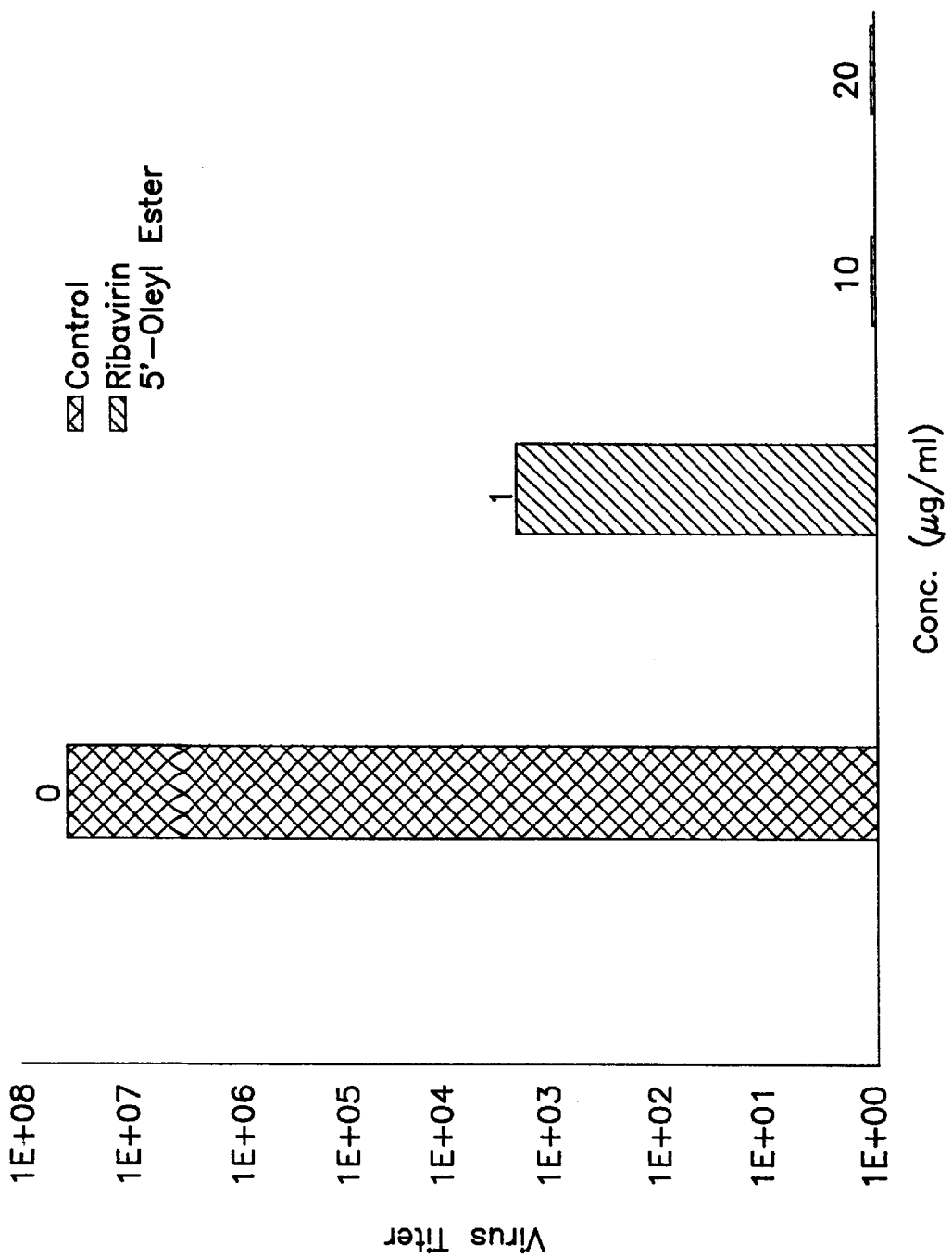
FIG. 1 is a graph showing the inhibitory effect of the oleic acid ester of ribavirin at three concentration levels.

It has now surprisingly been found that a selected group of fatty acid esters of anti-viral nucleoside analogues, wherein the fatty acid is a mono-unsaturated C18 or C20 acid, gives a much improved effect.

Although it is known that both nucleosides and nucleoside analogues, by themselves, and also some unsaturated fatty acids, by themselves, exhibit anti-viral effects, the magnitude of the effects achieved with the compounds according to this invention indicates that the effects are not additive, but rather there is synergistic activity which is special for the compounds of formula I. The mechanism behind these effects is at present not known. It is not considered likely that they arise only due to a membrane effect or targeting effect.

Further, it is also clear, as will appear from the biological examples included herein, that effects are achieved with these compounds in systems where lower effects may be achieved with the mother nucleoside compound.

The compounds of this invention can be characterized by the general formula I:

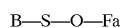

wherein O is oxygen, B—S is a nucleoside analogue in which B represents an optionally substituted heterocyclic ring system and S is a monosaccharide derivative, and Fa is an acyl group of a mono-unsaturated C18 or 20 fatty acid.

The natural nucleosides, named so with reference to their presence in RNA and DNA, are molecules comprising a heterocyclic base, such as cytosine, uracil, thymine, adenine or guanine, linked to a ribose or a 2-deoxy-ribose unit. In nucleoside analogues, either The base or the ribose unit has been modified. For example, the ribose unit may be replaced by another sugar unit or by a noncyclic chain.

A modified base may either be referred to as a compound selected from the groups of pyrimidines or purines, substituted differently than the herein mentioned natural bases, or as optionally substituted hetero-(mono or poly)cyclic ring systems, not being a pyrimidine or a purine.

The fatty acid is esterified with a hydroxyl group of the sugar moiety of the nucleoside analogue or with a hydroxyl group on the non-cyclic group of the nucleoside analogue. The nucleoside analogues which may be chosen as B—S in the compounds of formula I may preferably be represented by the formula II:

wherein S' is either a mono-saccharide-derivative selected from: 1-β-D-ribofuranose, 1-β-D-arabinofuranose, 2-deoxy-1-β-D-ribofuranose, 2,3-dideoxy-1-β-D-ribofuranose, 2,3-didehydro-2,3-dideoxy-1-β-D-ribofuranose, 2-deoxy-2-fluoro-1-β-D-arabinofuranose, 2,3-di-deoxy-3-azido-1-β-D-ribofuranose or 4-hydroxymethyl-2-cyclopenten-1-yl, or selected from the group of 2-hydroxy-ethoxy-methyl, 4-hydroxy-3-(hydroxymethyl)-butyl, 2-hydroxy-1-(hydroxy-methyl)-ethoxy-methyl, 2,3-di-hydroxy-propoxy or 2,3-di-hydroxy-propyl; and B' is a heterocyclic ring system selected from:

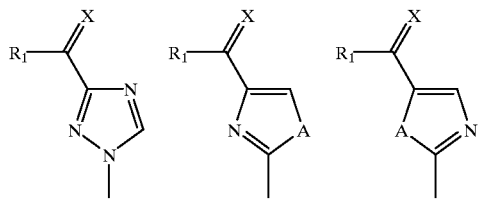
(i)
wherein X=O, S, NH and R$_1$=NH$_2$, CH$_3$, CH$_3$O and A=NH, S, Se, CH$_2$, O.
or
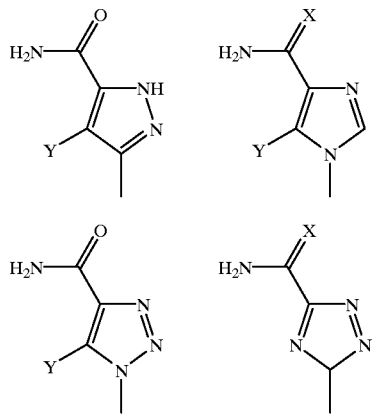
(ii)
wherein X=NH, S, O and Y=H, OH, F, Cl, Br, I, NH$_2$, CH$_2$CN, C≡CH or
(iii)
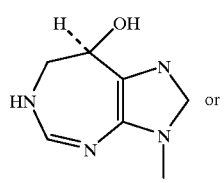
or
(iv)
wherein R$_4$=H, NH$_2$, NHOH, NHCOCH$_3$, NHCH$_2$, NHNH$_4$ and R$_5$=H, F, Cl, Br, I, CH$_2$, CF$_3$ and R$_4$=CH$_3$ F, I, CH=CHBr, CH$_2$OH, CH$_2$NH$_2$, C≡CCH$_4$
or
(v)
wherein R$_2$=OH, SH, H, Cl and R$_3$=H, OH, Cl, SH, NH$_2$
Examples of these nucleoside analogues are:
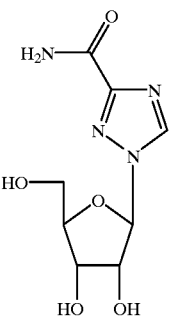
III
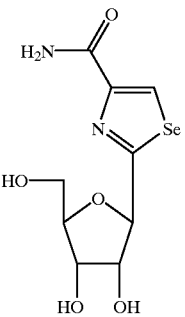
IV
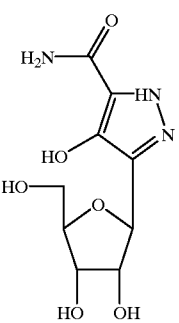
V
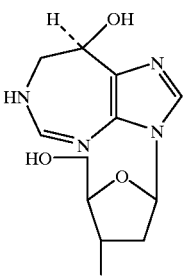
VI III=1-β-D-ribofuranosyl-1,2,4-triazole-3-carboxamide (Ribavirin), IV=2-β-D-ribofuranosylselenazole-4-carboxamide (Selenazole), V=4-hydroxy-3-β-D-ribofuranosylpyrazole-5-carboxamide (Pyrazofurin, Pyrazomycin), VI=2'-deoxy-coformycin.

Examples of other nucleoside analogues are:

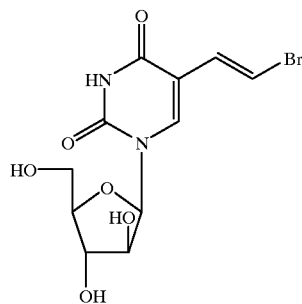

VII

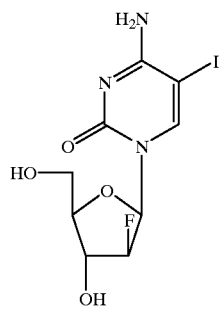

VIII

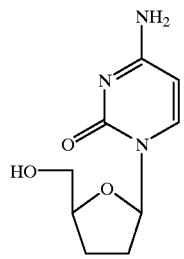

IX

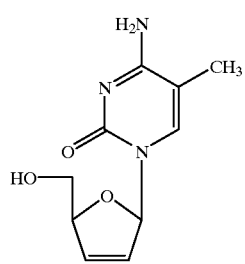

X

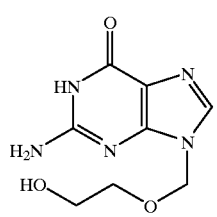

XI

VII=BVAU, VII=FIAC, IX=ddC, X=D4T and:

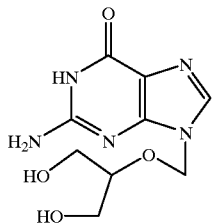

XII

XI=Acyclovir, XII=Ganciclovir

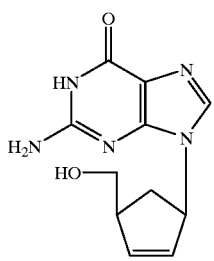

XIII

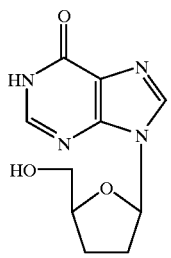

XIV

XIII=Carbovir, XIV=ddI
and:

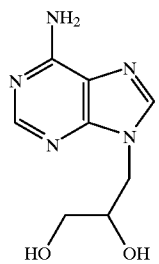

XV

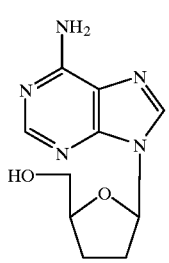

XVI

XV=(S)-DHPA, XVI=ddA

Of the compounds listed, the fatty acid esters of VI (2'-deoxy-coformycin) are of particular interest in the treatment of cancer, while the fatty acid esters of V (Pyrazomycin) can be used as antibiotics.

There exist several systems for denomination of the position of double bonds in fatty acids. In the present application the ω-system is used, wherein the position of the double bond in the unsaturated fatty acids is counted from the terminal methyl group. Eicosenic acid (C20:1 ω-9), for example, has 20 carbon atoms in the chain, and the double bond is found between carbon atom 9 and 10 counting from the end of the chain.

The selected group of fatty acids which may be reacted with the nucleoside analogues to form the esters according to this invention with the pronounced activity, have been found to be only C18 or C20 monounsaturated fatty acids. Further, even though the effect observed differs somewhat between acids of the same chain length when the double bond is in cis or trans configuration, both show a strong activity.

The C18 or C20 ω-9 fatty acids, which bound to the nucleoside analogues give the surprisingly elevated effect, are the following: oleic acid (C18:1, ω-9, cis), elaidic acid (C18:1, ω-9, trans) eicosenic acid, (C20:1, ω-9, cis) and (C20:1, ω-9, trans)

Preferred representatives of the compounds according to this invention are listed below.: Ribavirin oleic acid ester, Ribavirin elaidic acid ester, Ribavirin cis-eicosenoic acid ester, Ribavirin trans-eicosenoic acid ester, Selenazole oleic acid ester, Selenazole elaidic acid ester, Selenazole cis-eicosenoic acid ester, Selenazole trans-eicosenoic acid ester, Pyrazomycin oleic acid ester, Pyrazomycin elaidic acid ester, Pyrazomycin cis-eicosenoic acid ester, Pyrazomycin trans-eicosenoic acid ester, 2'-deoxy-coformycin oleic acid ester, 2'-deoxy-coformycin elaidic acid ester, 2'-deoxy-coformycin cis-eicosenoic acid ester, 2'-deoxy-coformycin trans-eicosenoic acid ester, d4T oleic acid ester, d4T elaidic acid ester, d4T cis-eicosenoic acid ester, d4T trans-eicosenoic acid ester, ddC oleic acid ester, ddC elaidic acid ester, ddC cis-eicosenoic acid ester, ddC trans-eicosenoic acid ester, ddI oleic acid ester, ddI elaidic acid ester, ddI cis-eicosenoic acid ester, ddI trans-eicosenoic acid ester, Carbovir oleic acid ester, Carbovir elaidic acid ester, Carbovir cis-eicosenoic acid ester, Carbovir trans-eicosenoic acid ester, (S)-DHPA oleic acid ester, (S)-DHPA elaidic acid ester, (S)-DHPA cis-eicosenoic acid ester, (S)-DHPA trans-eicosenoic acid ester, BVARAU oleic acid ester, BVARAU elaidic acid ester, BVARAU cis-eicosenoic acid ester, BVARAU trans-eicosenoic acid ester, BVDU oleic acid ester, BVDU elaidic acid ester, BVDU cis-eicosenoic acid ester, BVDU trans-eicosenoic acid ester, FIAC oleic acid ester, FIAC elaidic acid ester, FIAC cis-eicosenoic acid ester, FIAC trans-eicosenoic acid ester, EICAR oleic acid ester, EICAR elaidic acid ester, EICAR cis-eicosenoic acid ester, EICAR trans-eicosenoic acid ester, 2'-F'ARA-Ribavirin oleic acid ester, 2'-F'ARA-Ribavirin elaidic acid ester, 2'-F'ARA-Ribavirin cis-eicosenoic acid ester, 2'-F'ARA-Ribavirin trans-eicosenoic acid ester. Their formulas will appear from FIG. 4.

The compounds according to this invention exhibit antiviral effects, and the present invention thus includes pharmaceutical or veterinary compositions comprising at least one compound of formula I alone or in combination with a pharmaceutically acceptable carrier or excipient. In the remainder of the text and in the claims, a pharmaceutical composition will be used for compositions usable in the treatment of both human and animal patients.

Further, it appears that certain of the monounsaturated fatty acid nucleoside analogues will be especially suitable for the treatment of certain viral infections. Thus it appears that the fatty acid esters according to this invention of Ribavirin are especially suitable for the treatment of herpes infections.

Similarly, it appears that the compounds of the present invention or compositions containing same are also useful in treating diseases in humans caused by adenoviruses, influenza A and B viruses, respiratory syncytical virus (RSV), cytomegalo virus (CMV), papilloma viruses, bunyaviruses, arenaviruses and HIV.

As mentioned, the production of the necessary immune response in order to conquer a viral infection, such as hepatitis, can be induced in some cases by the co-administration of interferon.

Further, it appears that the fatty acid esters according to this invention or compositions containing the same are also useful in treating non-human mammals, birds, e.g., chickens and turkeys, and cold-blooded animals, e.g. fish, suffering from infections caused by: Bovine 1,2,3,4, Equine herpesvirus 1,2,3, Pig herpesvirus 1,2, Phasianine herpesvirus 1,2 (Marek's disease) and IPN (Infectious Pancreas Necrosis) virus.

Depending on which viral infection is to be treated and at what stage the infection is, or if the patient is a human being or an animal, both a systemic and a local administration of the compounds can take place. For local administration, the compounds can be formulated as known in the art for administration to the skin or mucosa in any suitable form.

When administrered topically the compounds of formula I may be formulated as an ointment, cream, gel, tincture, spray, lotion or the like containing the compounds of formula I in admixture with inert, solid or liquid carriers which are usual in topical preparations. It is especially suitable to use a formulation which protects the active ingredient against oxidation or degradation.

The pharmaceutical preparations comprising the compounds of formula I may also be administrered systemically, either enterally or parenterally.

When administrered enterally, the compounds of formula I may be formulated e.g. as soft or hard gelatin capsules, tablets, granules, grains or powders, dragees, syrups, suspensions or solutions.

When administrered parenterally, preparations of the compounds of formula I as injection or infusion solutions, suspensions or emulsions are suitable.

The preparations can contain inert or pharmacodynamically active additives. Tablets or granulates e.g. can contain a series of binding agents, filler materials, carrier substances or diluents. Liquid preparations may be present, for example, in the form of a sterile solution. Capsules can contain a filler material or thickening agent in addition to the active ingredient. Furthermore, flavour-improving additives as well as the substances usually used as preserving, stabilizing, moisture-retaining and emulsifying agents, salts for varying the osmotic pressure, buffers and other additives may also be present.

The dosages in which the preparations according to this invention are administered will vary according to the mode of use and the route of use, as well as to the requirements of the patient. In general a daily dosage for a systemic therapy for an adult average patient or an animal will be about 0.1–100 mg/kg body weight/day, preferably 1–20 mg/kg/day. For topical administration, the suitable ointment can contain from 0.1–10% by weight of the pharmaceutical formulation, especially 0.5–5% by weight.

If desired the pharmaceutical preparation of the compound of formula I can contain an antioxidant, e.g. tocopherol, N-methyl-tocopheramine, butylated hydroxyanisole, ascorbic acid or butylated hydroxytoluene.

The invention further discloses a method for the treatment of viral infections, which comprises administering at least one compound of formula I to a human or animal patient in need of such treatment.

Further, the invention also comprises a method for the treatment of a patient in need of such treatment with a combination of a compound of formula I and an interferon.

BIOLOGICAL EFFECTS

Tissue culture of IPN virus.

A preparation of IPN Virus (1000 pfu) is inoculated and incubated with shaking for 1 hour at 20° C. on a monolayer of CHSE-214 cells. To the cells are added a small volume of a growth medium containing an anti viral agent. The cells are then cultivated (48 h) until positive obsevation of CPE in the untreated control. Thereafter, the cells are placed under freezing conditions overnight. Following thawing and centrifugation, the supernatant is added at 5 dilution levels to a monolayer of a freshly prepared cell culture in a 96 well tray. CPE is registered after 48 h, and the virus titer is calculated as $TCID_{50}$.

FIG. 1 shows the inhibitory effect of the oleic acid ester of ribavirin at three concentration levels. The virus is completely eradicated at the two high dose levels, and the reduction in the virus titer is at the order of $10^4$ even at the low concentration.

A. IN VITRO EXPERIMENTS

The Plague Method

Tissue Culture of HSV 1/2 Virus

Virus preparations of HSV 1 and HSV 2 (3rd passage of a clinical isolate) are diluted to 250 and 100 pfu/well respectively, and thereafter, cells are inoculated with the virus preparation and the virus preparation is then incubated for 1 hour in a tissue culture with various cell lines. The infected cells are then cultivated for 48 hours with an anti-viral agent. The cultures are frozen and thawed to liberate free virus. Dilutions of either 1/100 or 1/10000 are prepared and added to fresh tissue cultures. After an incubation for 1 hour, Carboxymethylcellulose (CMC) is added in order to prevent migration of virus between the cells through the medium. Spread of virus by cell contact is still effective causing the formation of plaques.

One plaque will represent one infectious virus. Thus the counting of plaques gives a precise quantitation of the number of infectious virus.

Figure 2:
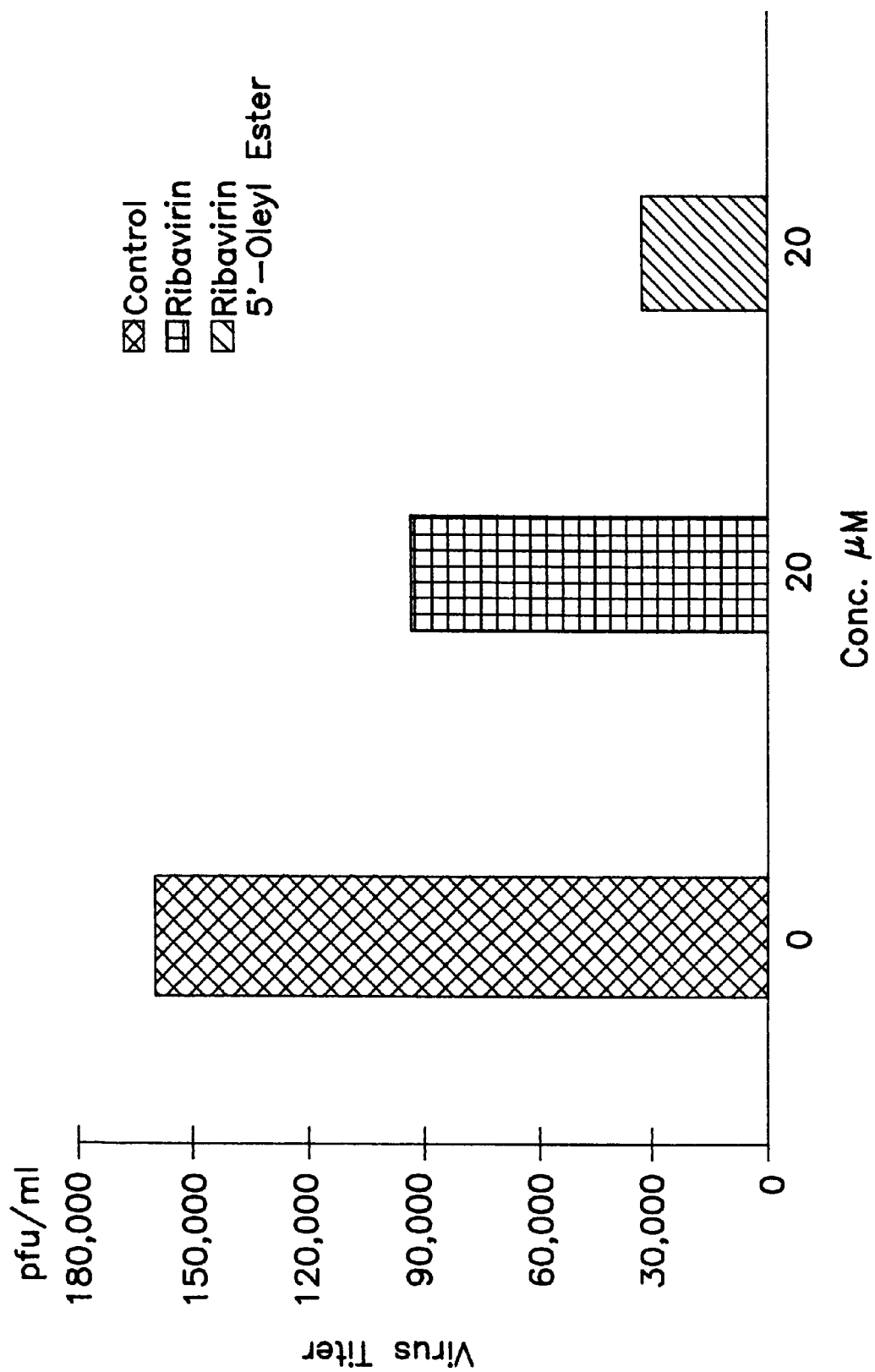
FIG. 2 is a graph showing the inhibitory effect of ribavirin and ribavirin 5'-oleyl ester.

FIG. 2 shows the inhibitory effect of ribavirin and ribavirin-5'-oleyl ester on a HSV 2 strain (68495) in a HL1 cell line. This virus strain is relatively resistant to ribavirin itself, as can be seen from the moderate reduction in virus titer. This resistance was even more evident with the other cell lines which were investigated. However, with the cell line to which FIG. 2 relates, it is seen even so that the introduction of the mono-unsaturated fatty acid ester group still potentiates the activity by a factor of 3.

B. IN VIVO EXPERIMENTS

FLC Virus Infection in Mice

Figure 3:
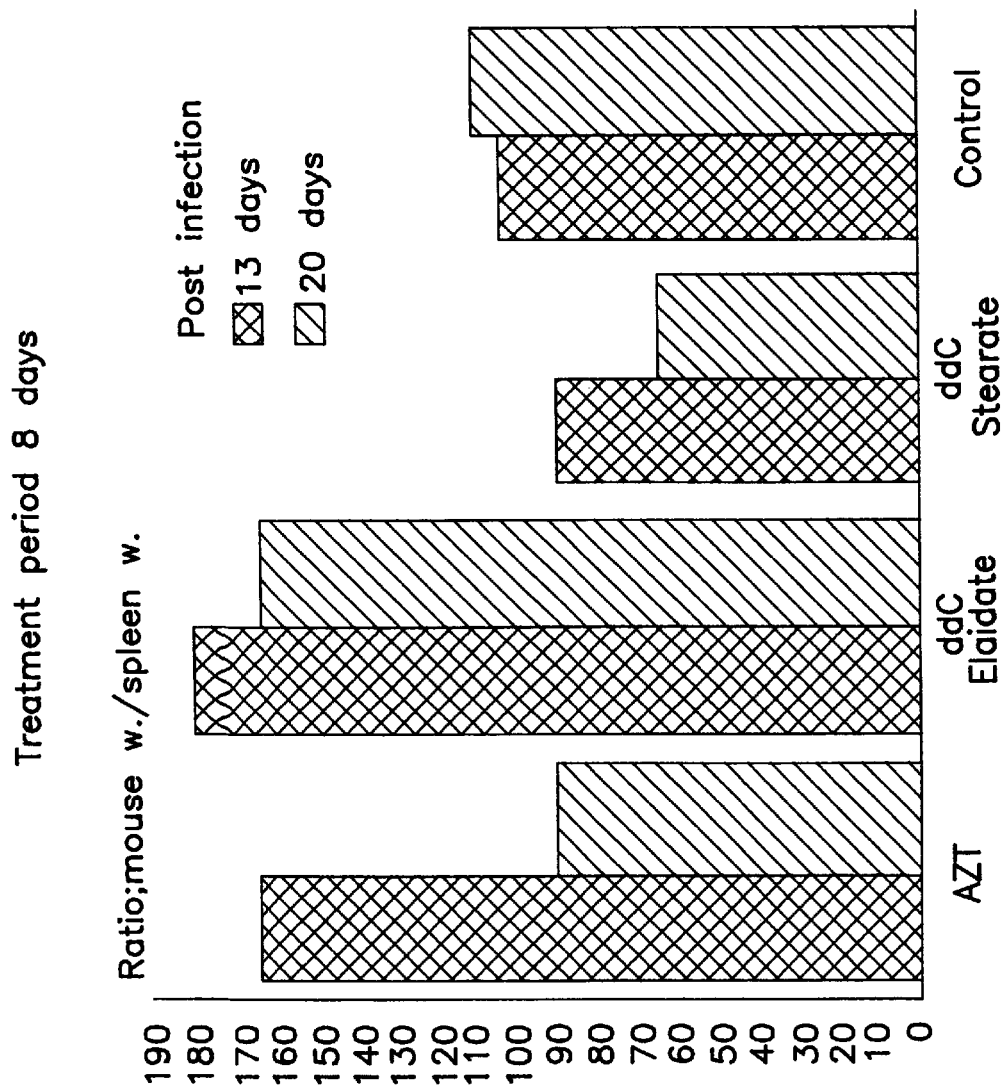
FIG. 3 is a graph comparing the effects of AZT, ddC elaidate and ddC stearate.
Figure 4A:
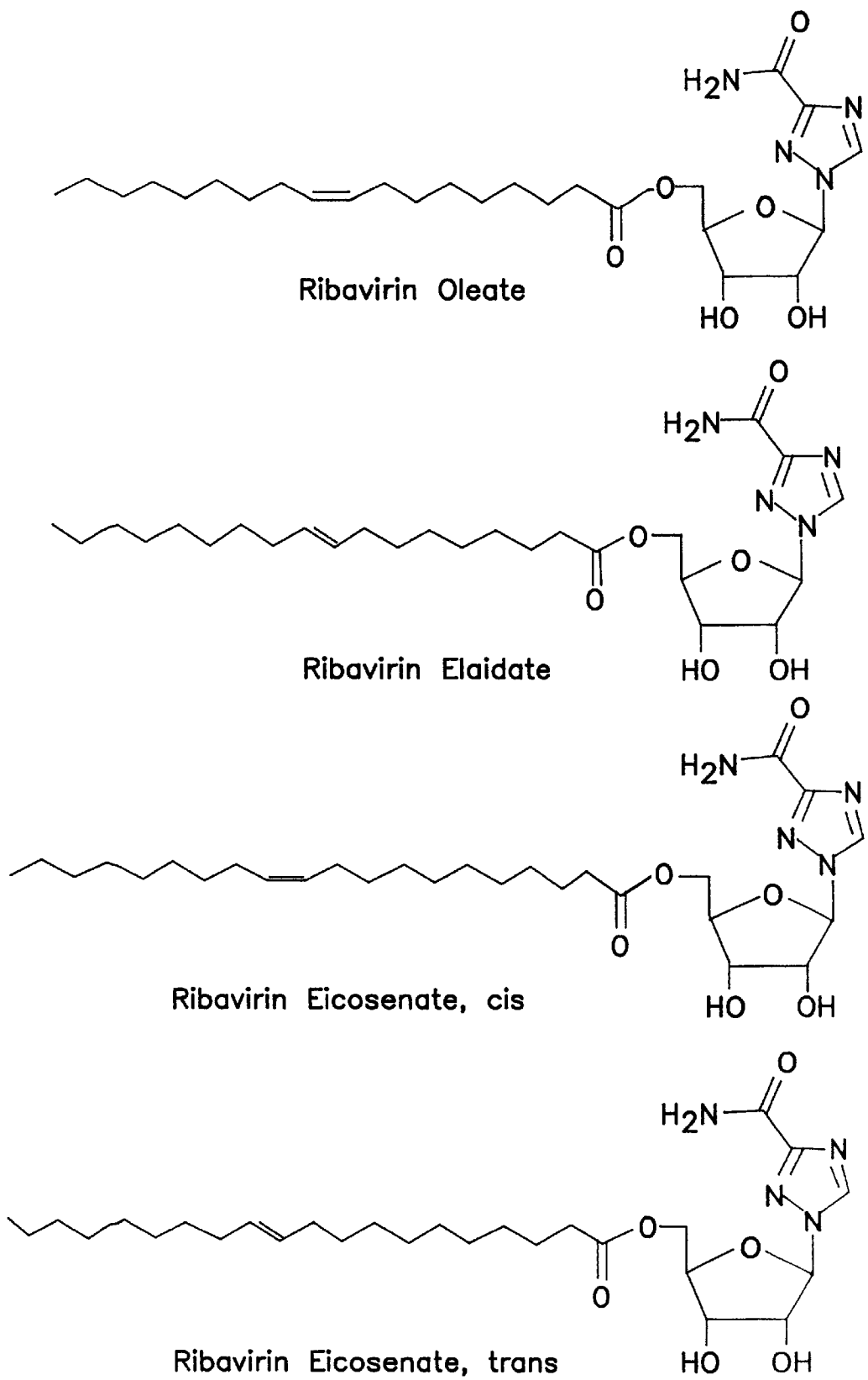
FIGS. 4A through 4N show structural formulas for fatty acid esters of nucleoside analogues.
Figure 4B:
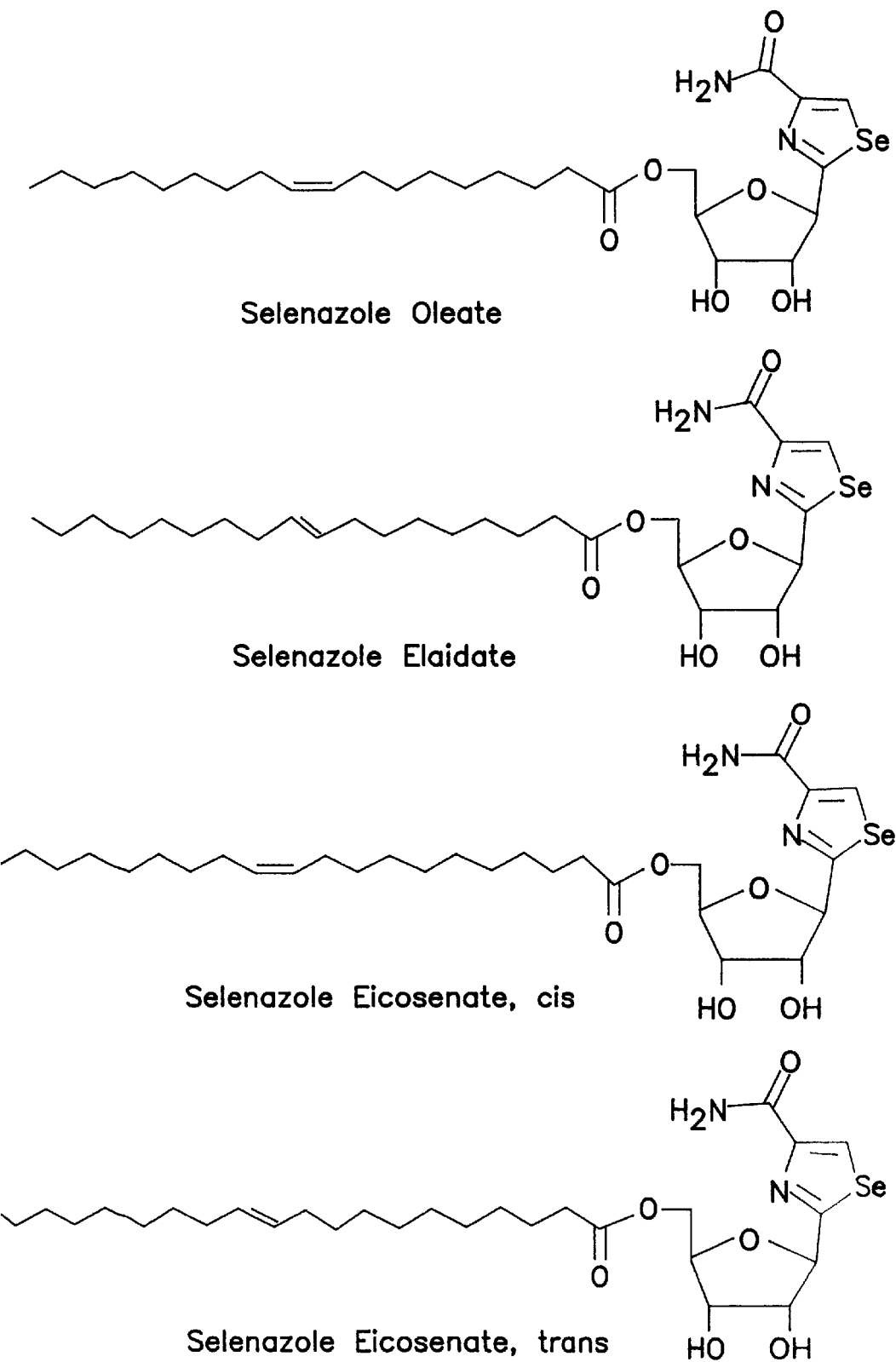
Figure 4C:
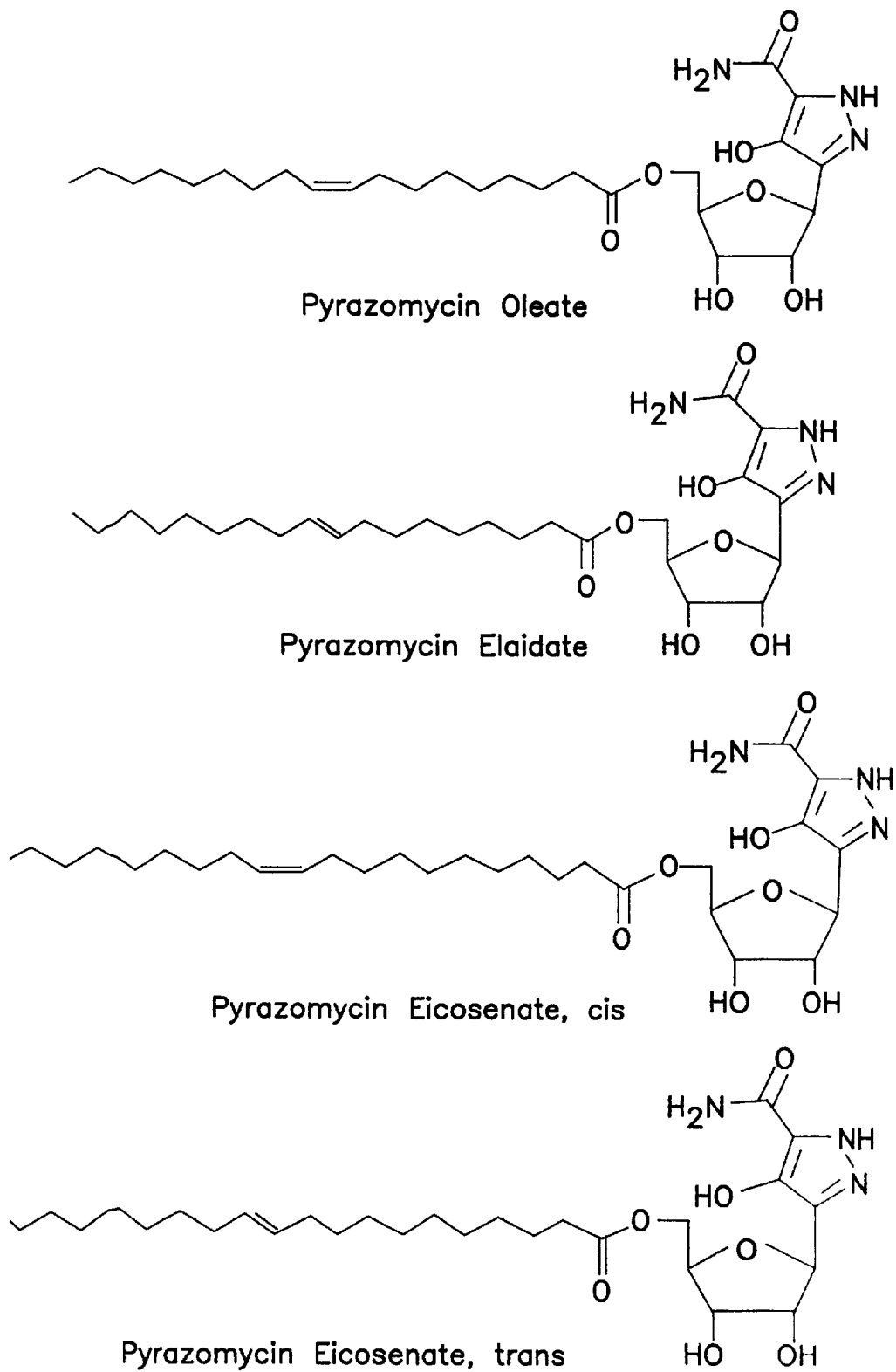
Figure 4D:
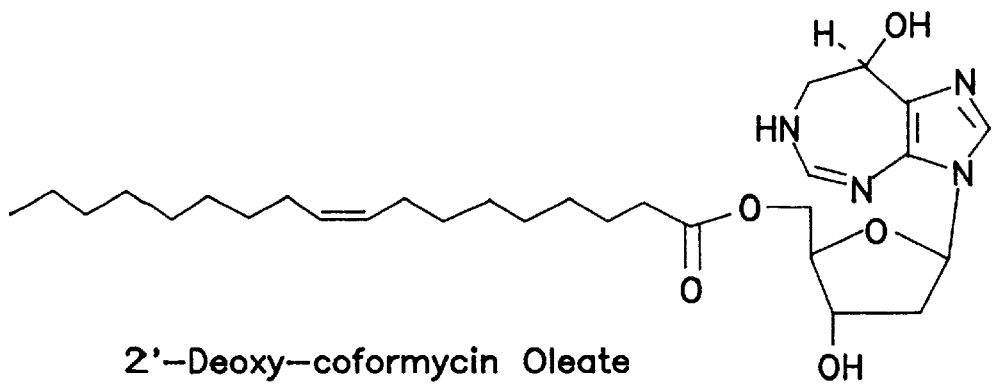
Figure 4D:
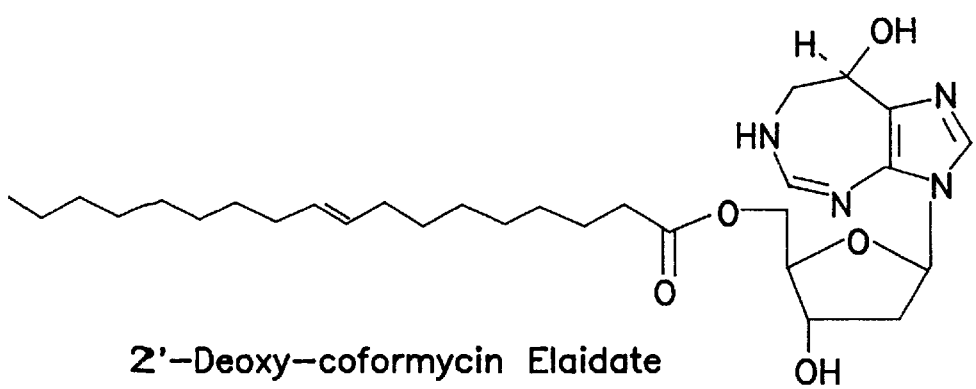
Figure 4D:
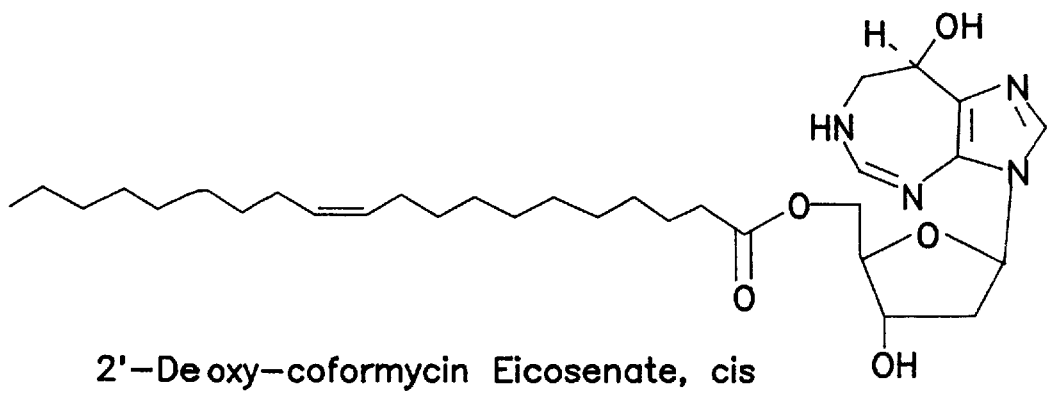
Figure 4D:
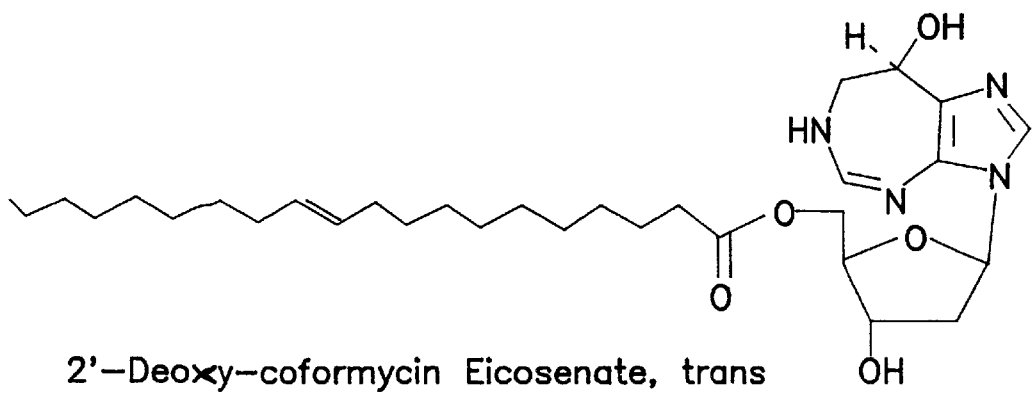
Figure 4E:
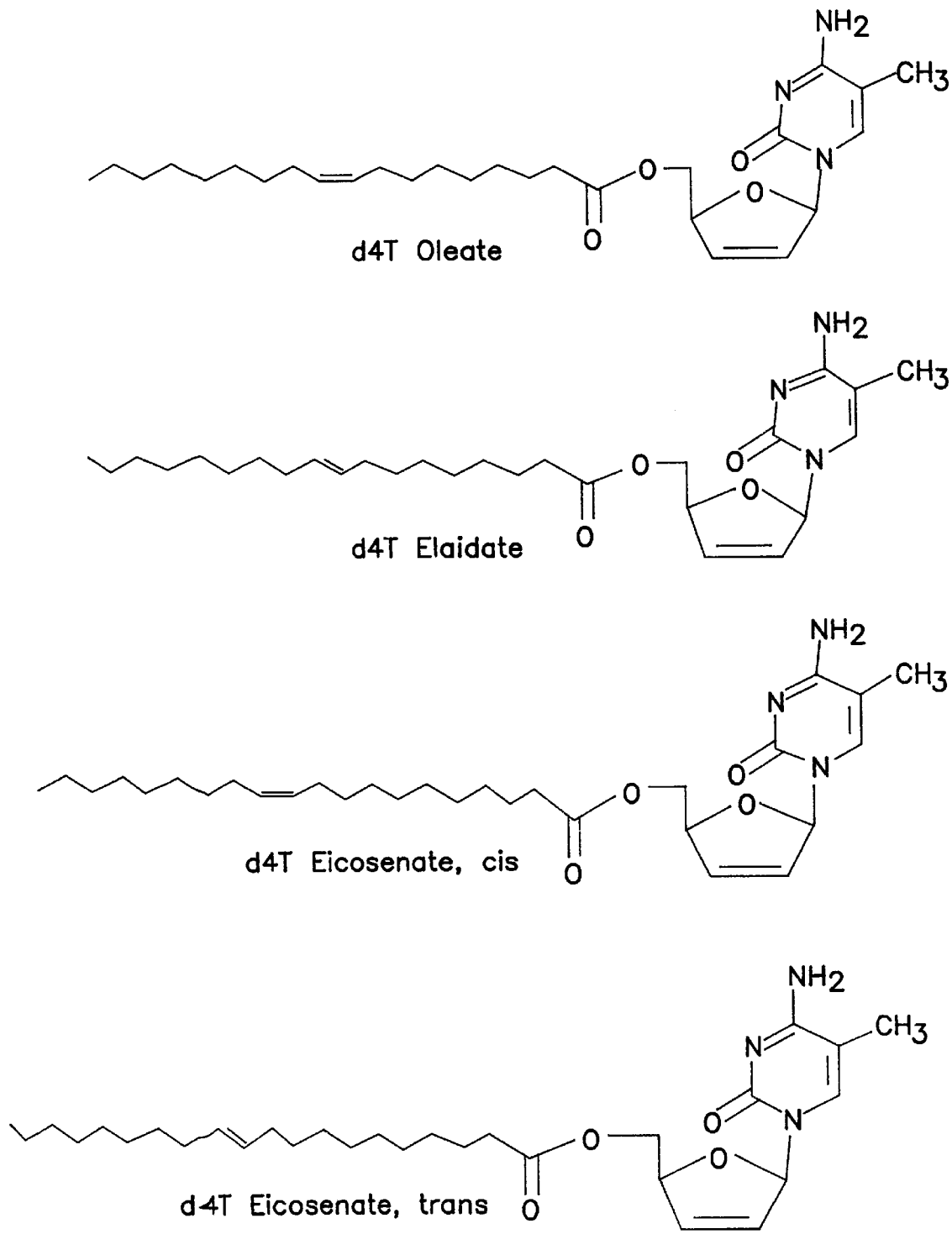
Figure 4F:
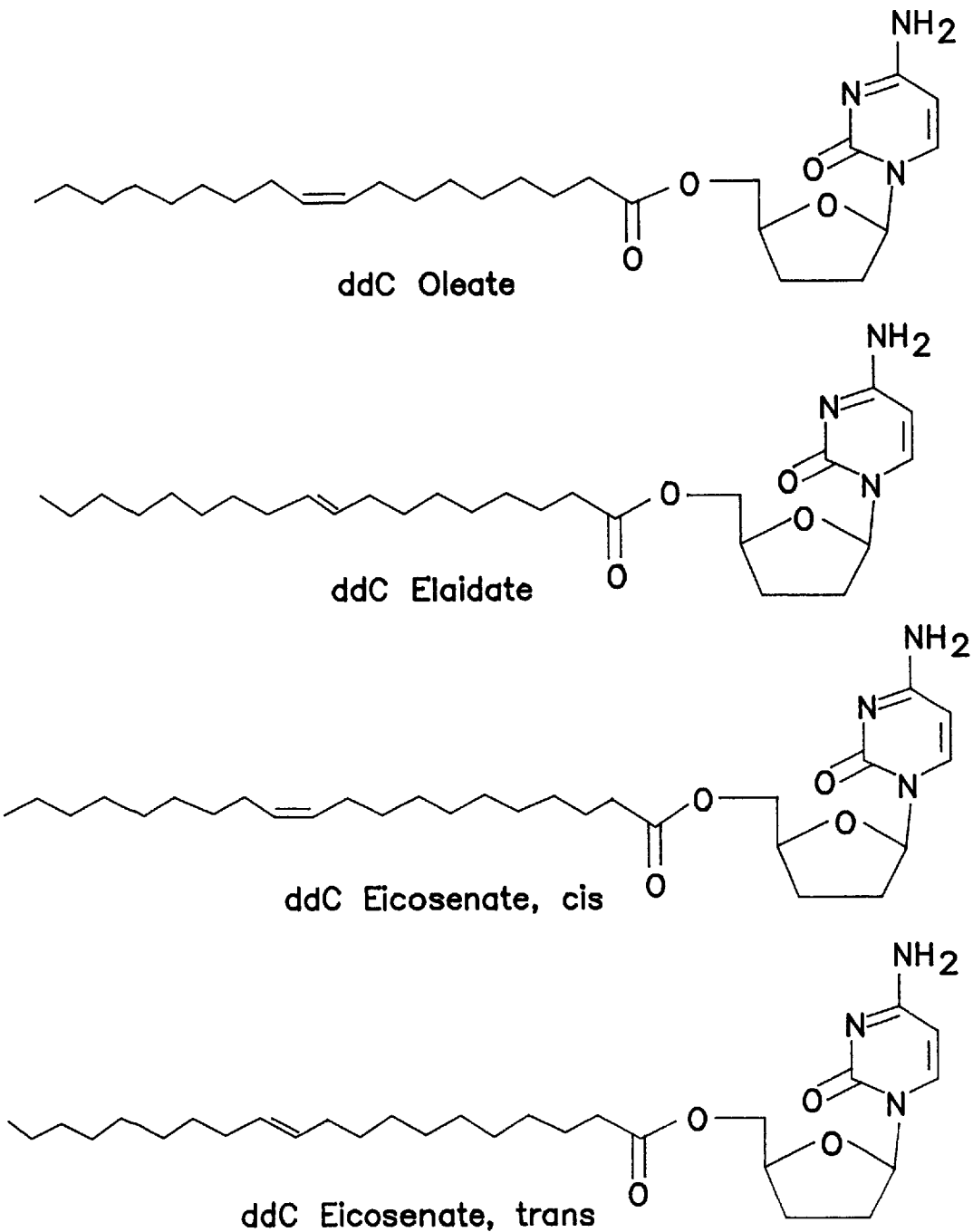
Figure 4G:
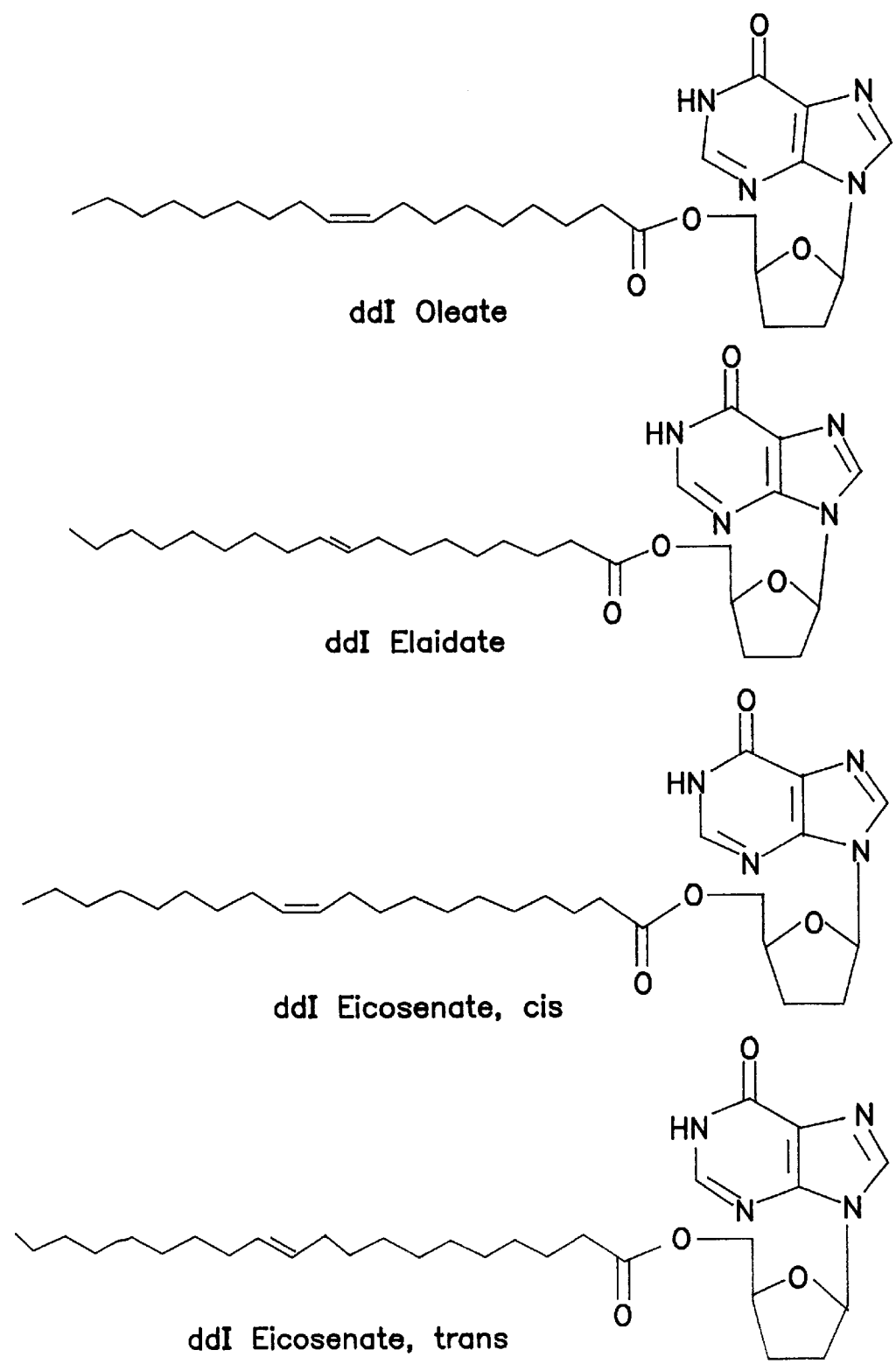
Figure 4H:
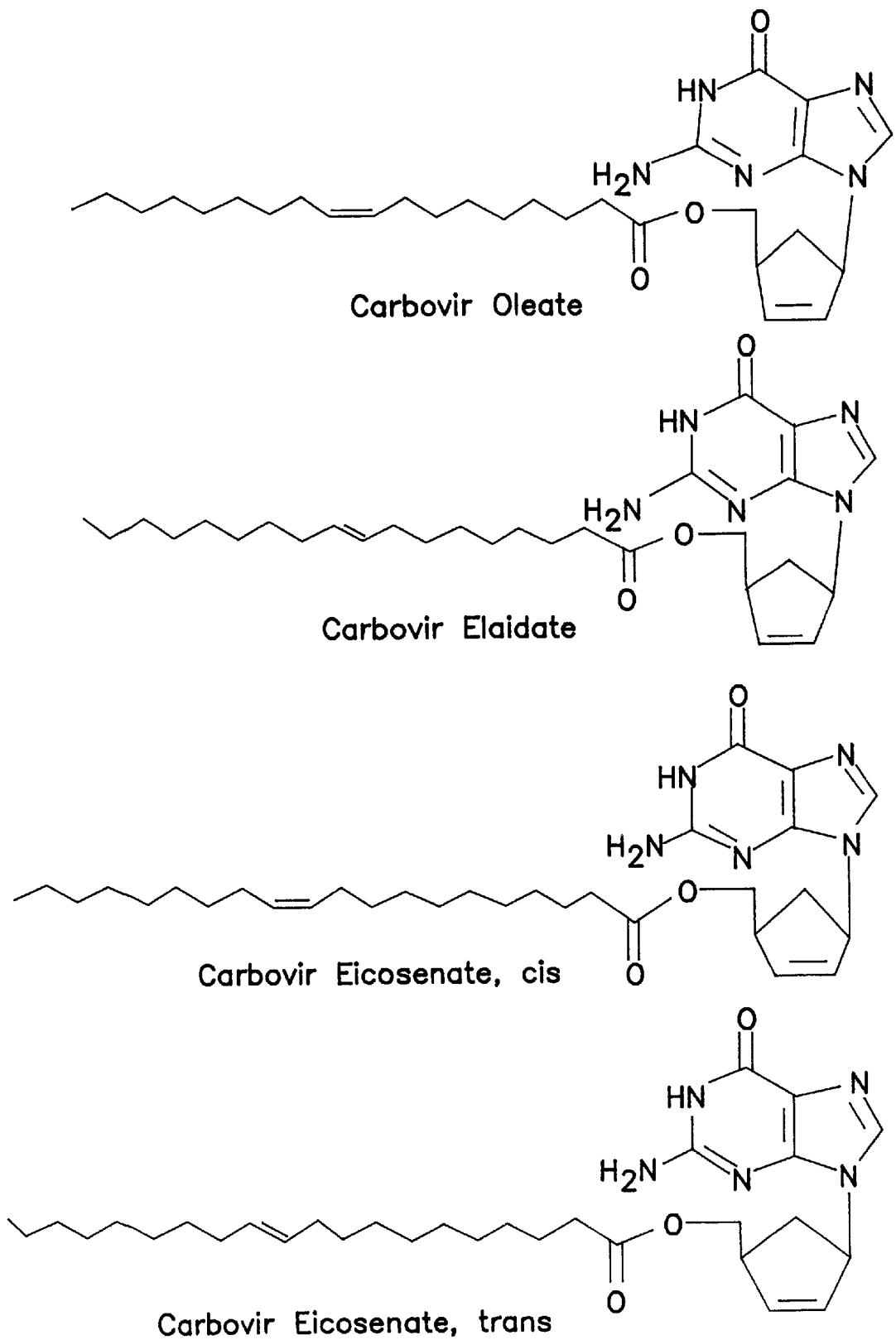
Figure 4I:
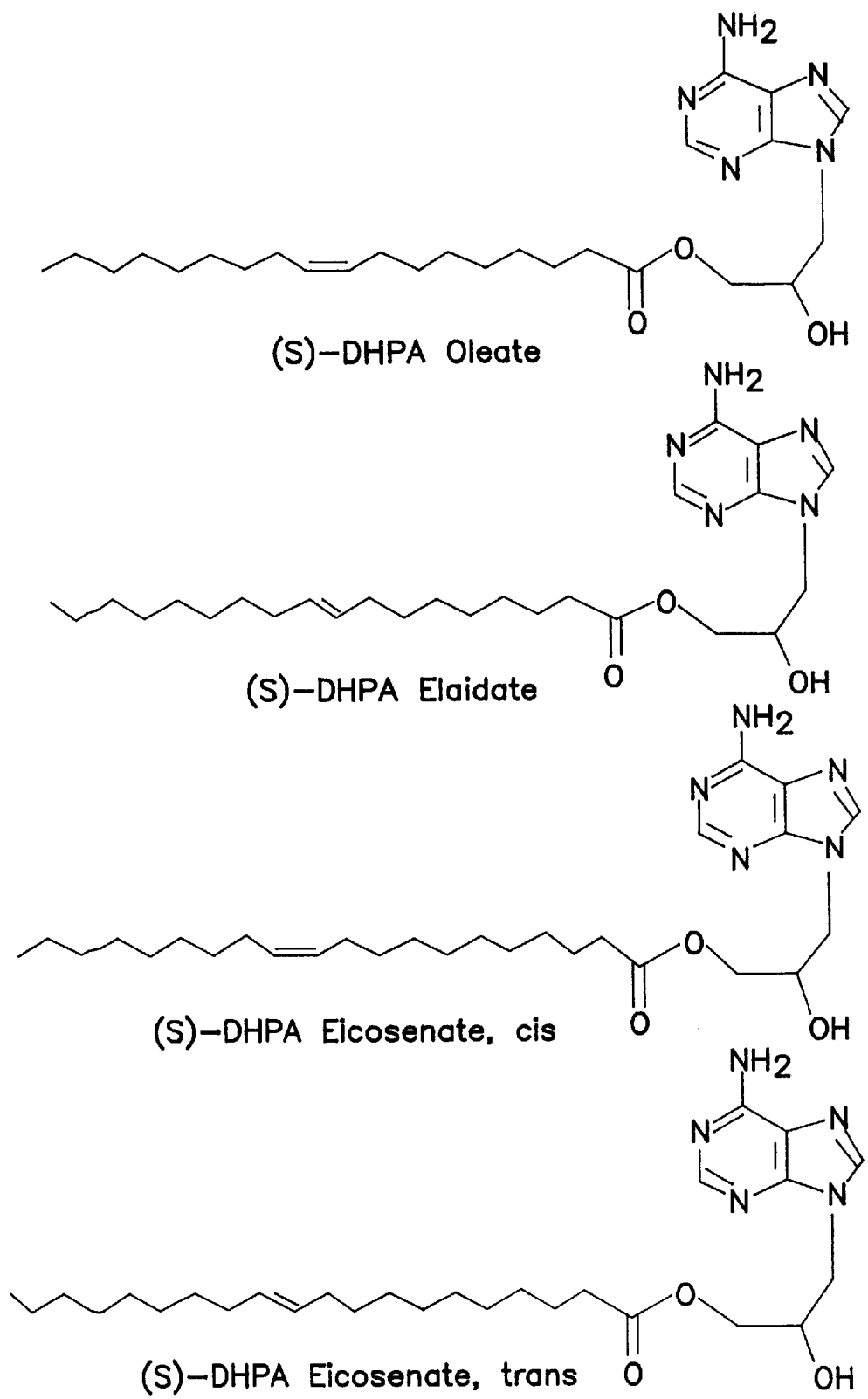
Figure 4K:
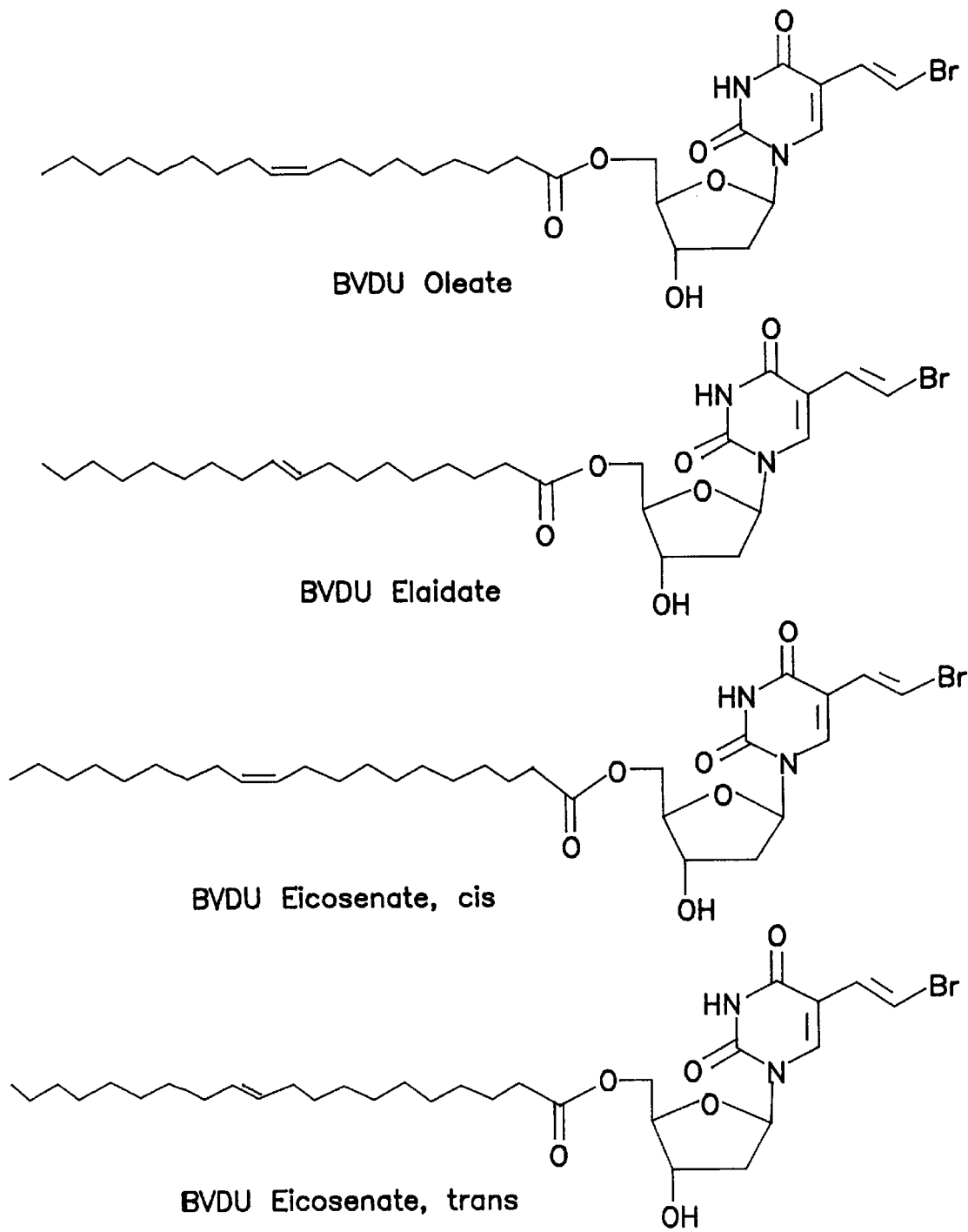
Figure 4L:
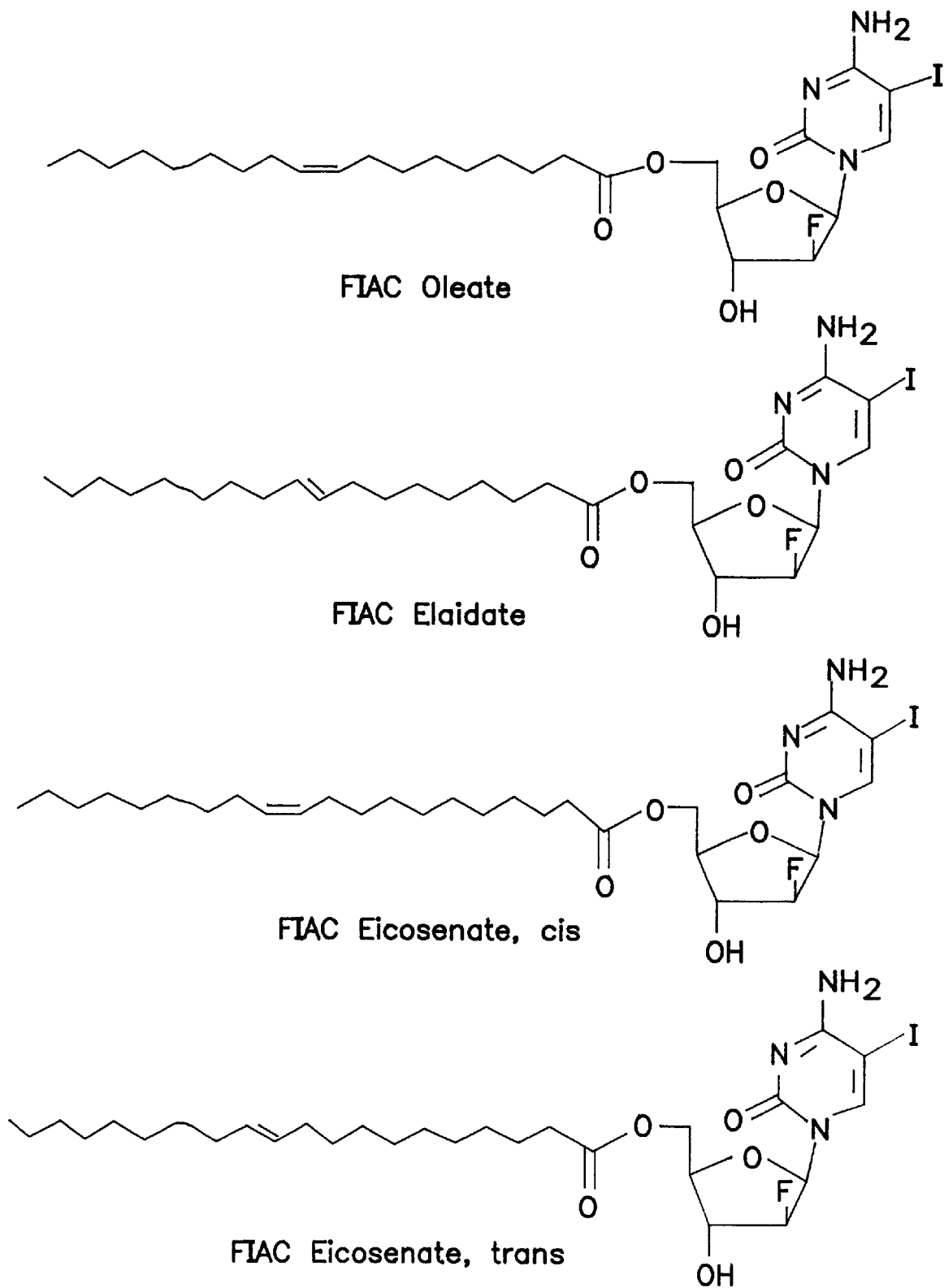
Figure 4M:
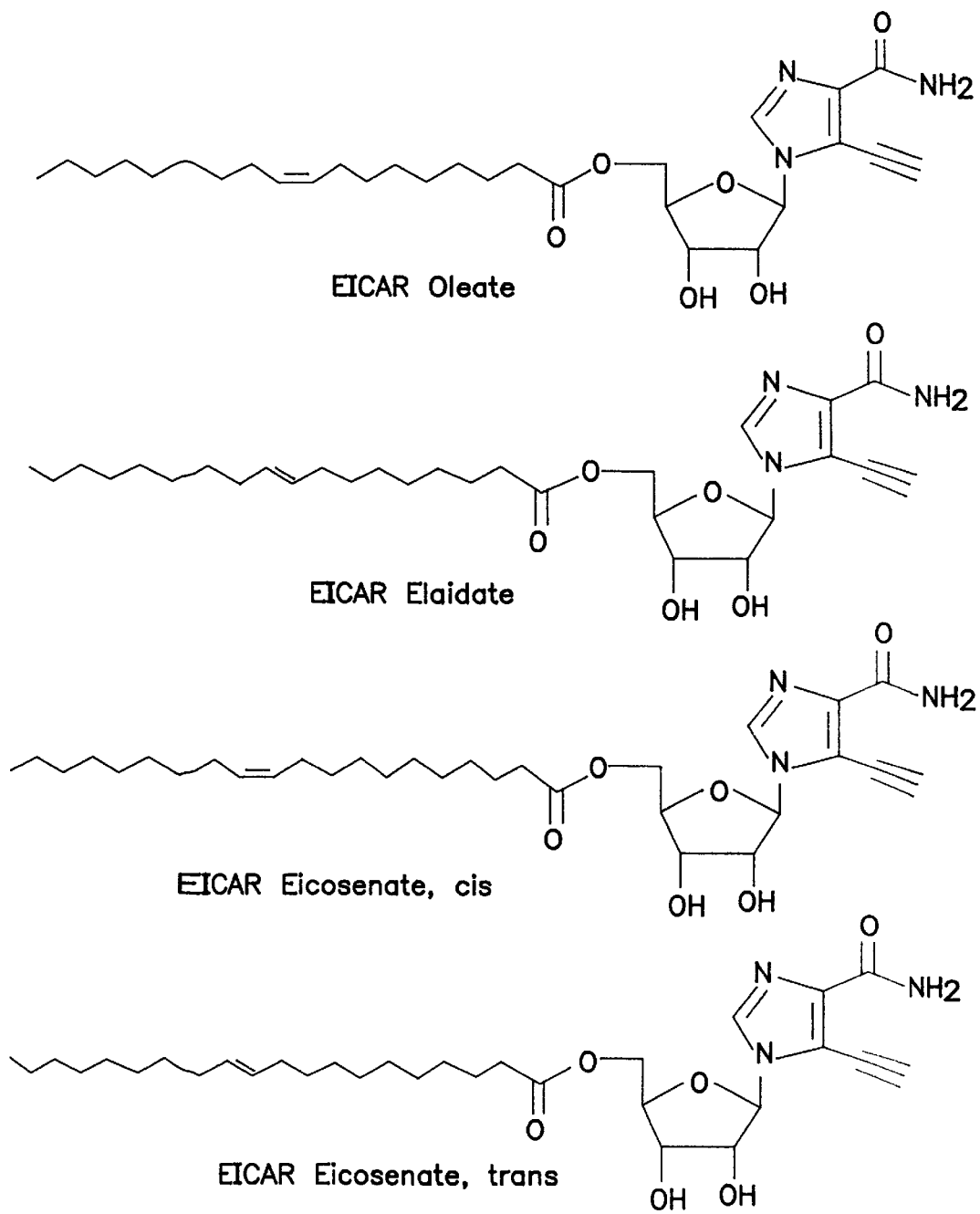

Young (20–25 g) female NMRI mice were infected i.p. with a preparation of the Friend Leukemia Complex (FLC) retrovirus. Treatment was started on day 2 from virus inoculation, and the animals received a daily dose of 200 µl of a 20 µM liposomal formulation of the test substances i.p. for 8 days. Groups of animals were killed 13 and 20 days post infection. The body and spleen weight of the animals was recorded. The FLC virus infection lead over a period of 7–10 days to a marked increase in the spleen weight, presumably due to a high concentration of leukemic cells. FIG. 3 shows a comparison of the effect of AZT, a leading drug in the treatment of retroviral induced infections, ddC elaidate and the corresponding saturated analogue e.g ddC stearate. The data is presented as the ratio; body weight/spleen weight, wherein a large number reflects high anti-retroviral effect. At 13 days the effect of AZT equaled the high value of ddC elaidate. After 20 days the ratios of the AZT treated animals dropped down to control level while the ddC elaidate treated animals retains a high ratio. The dependence of the nature of the fatty acid is evident, as can be seen from the low (–control) values of the stearic acid derivative.

The anti viral agents according to this invention were prepared as a 1 mg/ml micellar stock solution in water by mixing of lecithin and the active ingredient in a 1:1 (w/w) ratio in sterile, distilled water.

PREPARATION

The compounds of formula I may generally be prepared according to the following reaction equation:

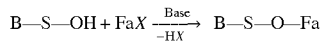

wherein B,S, O and Fa are as defined above, and X may be Cl, Br, O—CO—R', wherein R' is Fa, $CH_3$, $CH_2CH_3$ or $CF_3$. X may also be the benzotriazole part of an fatty acid benzotriazole ester.

Thus the reaction proceeds by acylation of the nucleoside analogue. This is accomplished by the use of suitable reactive derivatives of the fatty acids, especially acid halides or acid anhydrides. The reactive derivatives of the fatty acids may be preformed or generated in-situ by the use of reagents such as dicyclohexyl-carbodiimide (DCC) or O—(1H-benzotriazol-1-yl)N,N,N',N',-tetramethyluroniumtetrafluoroborate (TBTU). When an acid halide such as an acid chloride is used, a tertiary amine catalyst, such as triethylamine, N,N-dimethylaniline, pyridine or N,N-dimethylaminopyridine is added to the reaction mixture to bind the liberated hydrohalic acid. The reactions are preferably carried out in an unreactive solvent such as N,N-dimethylformamide or a halogenated hydrocarbon, such as dichloromethane. If desired any of the above mentioned tertiary amine catalysts may be used as solvent, taking care that a suitable excess is present. The reaction temperature can be varied between 0° C. and 40° C., but will preferably be kept between 5° C. and 25° C. After a period of 24 to 60 hours, the reaction will be essentially completed. The progress of the reaction can be followed using thin layer chromatography (TLC) and appropriate solvent systems. When the reaction is completed as determined by TLC, the product is extracted with an organic solvent and purified by chromatography and/or recrystallisation from an appropriate solvent system. If more than one hydroxyl group or also amino groups are present in the nucleoside analogue, a mixture of acylated compounds may be produced. The individual mono- or polyacylated compounds may be separated by for instance chromatography.

The invention is illustrated by the non-limiting Examples which follow.

EXAMPLE 1

1-(5'-O-[cis-9"-Octadecenoyl]-β-D-Ribofuranosyl)-1,2,4-triazole-3-carboxamide.

To a solution of 1-β-D-ribofuranosyl-1,2,4-triazole-3-carboxamide (ribavirin) (0.95 g, $3.9 \times 10^{-3}$ mol) in 10 ml anhydrous N,N-dimethylformamide and 15 ml pyridine was added 2 ml of a stock solution of cis-9-Octadecenoylchloride (1.34 g, $4.7\times10^{-3}$ mol) in 6 ml dichloromethane, and the reaction mixture was stirred under nitrogen at room temperature. The remaining stock solution was added in 2 ml portions at approx. 8 h intervals. After a total of 60 hours reaction time, the solvents were evaporated at high vacuum, and the product was purified on a column of silica gel with 15% methanol in chloroform as the eluent system. Homogenous fractions were evaporated to give 1.25 g (63%) of the title compound as a white solid.

$^1$H NMR (DMSO-d$_6$, 300 MHz) δ: 9.8(1H,s,H-5), 7.85 and 7.65(1+1H,s,NH$_2$), 5.88(1H,d,H-1'), 5.65(1H,d,OH-2'), 5.35(1H,d,OH-3'), 5.32(2H,m,CH=CH), 4.35–4.25(3H,m, H-2',H-3',H-5'$_1$), 4.15–4.0(2H,m,H-4',H-5'$_2$), 2.25(2H,t, CH$_2$—COO), 1.95(4H,m,CH$_2$—C=), 1.45(2H,m,CH$_3$—C—COO), 1.25(20H,m,CH$_2$), 0.85(3H,t,CH$_2$—CH$_2$).

$^{13}$C NMR (DMSO-d$_6$, 75 MHz) δ: 172.59(COO), 160.15 (CONH$_2$), 157.40(C-3), 145.27(C-5), 129.46(CH=CH), 91.28(C-1'), 81.51(C-4'), 73.99(C-2'), 70.26(C-3'), 63.55(C-5'), 33.07, 31.13, 28.94, 28.68, 28.54, 28.43, 28.33, 28.24, 26.42, 24.17, 21.94(CH$_2$), 13.78(CH$_3$—CH$_2$).

EXAMPLE 2

1-(5'-O-[trans-9''-Octadecenoyl]-2,3-Dideoxy-β-D-glycero-pent-2-enofuranosyl)thymine.

To a solution of 1-(2,3-Dideoxy-β-D-glycero-pent-2-enofuranosyl)-thymine (d4T) (0.83 g, $3.7\times10^{-3}$ mol) in 10 ml anhydrous N,N-dimethylformamide and 10 ml pyridine was added 2 ml of a stock solution of trans-9-Octadecenoylchloride (1.39 g, $4.9\times^{-3}$ mol) in 4 ml dichloromethane, and the reaction mixture was stirred under nitrogen at room temperature. The remaining stock solution was added in 1 ml portions at approx. 8 h intervals. After a total of 60 hours reaction time, the solvents were evaporated at high vacuum. The residue was dissolved in chloroform and washed with water. The dried (MgSO$_4$) organic phase was concentrated, and the crude product was purified on a column of silica gel with 7% methanol in chloroform as the eluent system. Homogenous fractions were evaporated to give 1.26 g (70%) of the title compound as a white solid.

$^1$H NMR (DMSO-d$_6$, 300 MHz) δ: 11.35(1H,s,NH), 7.25(1H,s,H-6), 6.81(1H,m,H-1'), 6.38(1H,m,H-3'), 6.0(1H, m,H-2'), 5.35(2H,m,CH=CH), 4.95(1H,m,H-4'), 4.2(2H,m, H-5'), 2.25(2H,m,CH$_2$—COO), 1.95(4H,m,CH$_2$—C=), 1.75(3H,s,CH$_3$), 1.45(2H,m,CH$_2$—C—COO), 1.25(20H,m, CH$_2$), 0.85(3H,t,CH$_3$—CH$_2$).

EXAMPLE 3

5-O-(9'-trans-Octadecenoyl)-2,3-dideoxy-cytidine

To a suspension of 2,3-dideoxy-cytidine (ddC) (1,2 g, $5.7\times10^{-3}$ mol) in 40 ml anhydrous N,N-dimethylformamide containing HCl (g) ($6.3\times10^{-3}$ mol), was added 1 ml of a stock solution of trans-9-Octadecenoylchloride (1.7 g, $6.0\times10^{-3}$ mol) in 6 ml dichloromethane, and the reaction mixture was stirred under nitrogen at room temperature. The remaining stock solution was added in 1 ml portions at approx. 3 h intervals. After a total of 60 hours reaction time, the solvents were evaporated at high vacuum. The residue was dissolved in chloroform and washed with water. The dried (MgSO$_4$) organic phase was concentrated, and the residue was dissolved in heptane. Addition of petroleum ether (40–60) afforded a white solid (0.7 g) that was collected in the cold. The filtrate was purified on a column of silica gel eluted with methanol (0–25%) in ethylacetate. Homogenous fractions were evaporated to give another 0.8 g of the title compound (1.5 g, 55%).

$^1$H NMR (DMSO-d$_6$, 300 MHz) δ: 7.63(1H,d,H-6), 7.1 (2H,d,NH$_2$), 5.95(1H,m,H-1'), 5.7(1H,d,H-5), 5.35(2H,m, CH=CH), 4.25–4.10(3H, m,H-4' and H-5'), 2.3(3H,m, H-2' and CH$_2$—COO), 2.0–1.6(7H,m,H-2',H-3' and CH$_2$—C=), 1.45(2H,m,CH$_2$—C—COO), 1.25(20H,m,CH$_2$), 0.85(3H,t, CH—CH$_2$).

$^{13}$C NMR (DMSO-d$_6$, 75 MHz) δ: 172.67(COO), 165.60 (CNH$_2$ 4), 155.04 (CO 2), 140.45(CH 6), 130.00(CH=CH), 93.62(CH 5), 85.84(C 1'), 77.84(C 4'), 64.87(C 5'), 33.38, 31.96, 31.30, 29.02, 28.96, 28.86, 28.74, 28.52, 28.46, 28.36, 24.40, 22.11(CH$_2$), 31.76, 25.47 (CH 2' and 3'), 13.90 (CH$_3$).

EXAMPLE 4

5'-O-(9'-trans-Octadecenoyl)-5-iodo-2'-deoxy-Uridine

To a solution of 5-iodo-2'-deoxy-uridine (1.0 g, $2.8\times10^{-3}$ mol) in 10 ml anhydrous N,N-dimethylformamide and 15 ml pyridine was added 1 ml of a stock solution of trans-9-Octadecenoylchloride (1.12 g, $3.95\times10^{-3}$ mol) in 4 ml dichloromethane, and the reaction mixture was stirred under nitrogen at room temperature. The remaining stock solution was added in 1 ml portions at approx. 4 h intervals. After a total of 50 hours reaction time, the solvents were evaporated at high vacuum, and the product was purified on a column of silica gel with 10% methanol in chloroform as the eluent system. Fractions containing the product were concentrated and the residue was recrystallized from ethanol to give 1.43 g (82%) of the title compound as a white solid.

$^1$H NMR (DMSO-d$_6$, 300 MHz) δ: 11.71(1H,s,NH), 7.95(1H,s,H-6), 6.08(1H,t,H-1'), 5.4(1H,d,OH-3'), 5.35(2H, m,CH=CH), 4.2(3H,m,H-3'and 5'), 3.95(1H,m,H-4'), 2.35 (2H,t, CH$_2$—COO), 2.15(2H,m,H-2'), 1.95(4H,m,CH$_2$—C=), 1.50(2H,m,CH$_2$—C—COO), 1.25(20H,m,CH$_2$), 0.85 (3H,t,CH$_3$—C).

$^{13}$C NMR (DMSO-d$_6$, 75 MHz) δ: 172.16(COO), 159.90 (C=O 4), 149.50(C=O 2), 143.89(C-6), 129.51(CH=CH), 84.43(C-4'), 83.65(C-1'), 69.66(C-3'), 69.21(C-5), 63.06(C-5'), 38.85(C-2'), 33.01, 31.45, 30.79, 28.51, 28.34, 28.22, 28.01, 27.92, 27.85, 27.46, 23.93, 21.60(CH$_2$), 13.43 (CH$_3$—C).

EXAMPLE 5

5-O-(9'-trans-Octadecenoyl)-2,3-dideoxy-inosine.

A solution of trans-9-Octadecenoic acid (0.33 g, $1.17\times10^{-3}$ mol), O-(1H-benzotriazol-1-yl)N,N,N',N'-tetramethyluroniumtetrafluoroborate (TBTU) (0.52 g, $1.6\times10^{-3}$ mol) and di-isopropyl-ethyl-amin (0.5 ml) in 6 ml anhydrous N,N-dimethylformamide was stirred under nitrogen at room temperature. 2,3-dideoxy-inosine (0.19 g, $0.8\times10^{-3}$ mol) was added and the reaction mixture was stirred for 60 hours. The solvent was removed at high vacuum and the residue was dissolved in chloroform and washed with water. The dried (MgSO$_4$) organic phase was concentrated, and the crude product was purified on a column of silica gel eluted with 15% methanol in chloroform. Homogenous fractions were evaporated to give 0.25 g (62%) of the title compound as a slightly brown, waxy solid.

$^1$H NMR (DMSO-d$_6$, 300 MHz) δ: 12.35(1H,s,NH), 8.22(1H,s,H-2), 8.05(1H,s,H-8), 6.25(1H,dd,H-1'), 5.32(2H, m,CH=CH), 4.35–4.10(3H,m,H-4' and H-5'), 2.45(2H,m, H-2'), 2.25(2H,m,CH$_2$—COO), 2.10(2H,m,H-3'), 1.95(4H, m,$CH_2$—C≡), 1.45(2H,m,$CH_2$—C—COO), 1.25(20H,m, $CH_2$), 0.85(3H, t,$CH_3$—C).

$^{13}$C NMR (DMSO-$d_6$, 75 MHz) δ: 172.65(COO), 156.57 (C-6), 147.68(C-3), 145.62(C-2), 138.07(C-8), 129.98 (C≡C), 124.38(C-5), 84.33(C-1'), 78.54(C-4'), 64.91(C-5'), 33.25, 31.94, 31.36, 28.99, 28.93, 28.84, 28.71, 28.50, 28.39, 28.32, 24.34, 22.09($CH_2$), 31.27, 26.00(CH 2' and 3'), 13.88($CH_3$).

EXAMPLE 6

(S)-9-(2-Hydroxy-3-O-[9'-trans-octadecenoyl] propyl)-adenine.

To a solution of (S)-9-(2,3-dihydroxypropyl)adenine (0.8 g, 3.8×10$^{-3}$ mol), trans-9-Octadecenoic acid (1.2 g, 4.25× 10$^{-3}$ mol) and N,N-dimethyl-amino-pyridine (50 mg) in 20 ml anhydrous N,N-dimethylformamide was added dicyclohexylcarbodiimid (0.83 g, 4.0×10$^{-3}$ mol), and the reaction mixture was stirred under nitrogen as room temperature for 40 hours. The solvent was evaporated at high vacuum and the residue was purified by repeated chromatography on a column of silica gel with 5–15% methanol in chloroform as the eluent system. One set of homogenous fractions were concentrated to give 0.7 g (38%) of the title compound as a white solid.

$^1$H NMR (DMSO-$d_6$, 300 MHz) δ: 8.12(1H,s,H-8), 8.05 (1H,s,H-2), 7.20(2H,br s, $NH_2$), 5.48(1H,d,OH 2'), 5.35(2H, m,CH═CH), 4.3(1H,m,H-1'), 4.15(3H,m,H-3' and H-1'), 3.95(1H,m,H-2'), 2.25(3H,t,$CH_3$—COO), 1.95(4H,m, $CH_2$—C═), 1.45(2H,m,$CH_2$—C—COO), 1.25(20H,m, $CH_2$), 0.85(3H, t, $CH_3$—C).

$^{13}$C NMR (DMSO-$d_6$, 75 MHz) δ: 172.69(COO), 155.94 (C-6), 152.30(C-2), 149.65(C-4), 141.48(C-8), 130.02 (CH═CH), 118.57(C-5), 66.52(C-2'), 65.44(C-3'), 46.10(C-1'), 33.48, 31.98, 31.31, 29.02, 28.87, 28.75, 28.60, 28.52, 28.40, 24.37, 22.13($CH_2$), 13.93($CH_3$).

From another set of fractions was obtained 0.35 g (20%) of the isomeric product (S)-9-(3-Hydroxy-2-O-[9'-trans-octadecenoyl]-propyl)-adenine.

$^1$H NMR (DMSO-$d_6$, 300 MHz) δ: 8.12(1H,s,H-8), 8.05 (1H,s,H-2), 7.20(2H,br s, $NH_2$), 5.35(2H,m,CH═CH) , 5.12 (1H,t,OH 3'), 4.35(1H,m,H-2'), 4.3(1H,m,H-1'), 4.05(1H,m, H-1'), 3.5(2H,m,H-3'), 2.15(2H,t,$CH_2$—COO), 1.95(4H,m, $CH_2$—C═) , 1.45(2H,m,$CH_2$—C—COO), 1.25(20H,m, $CH_2$), 0.85(3H,t,$CH_3$—C)

$^{13}$C NMR (DMSO-$d_6$, 75 MHz) δ: 172.17(COO), 155.96 (C-6), 152.41(C-2), 149.78(C-4), 141.11(C-8), 130.02 (CH═CH), 118.52(C-5), 72.26(C-2'), 60.16(C-3'), 43.21(C-1'), 33.49, 31.99, 31.32, 29.02, 28.88, 28.75, 28.53, 28.35, 24.21, 22.13($CH_2$), 13.93($CH_3$).

EXAMPLE 7

5'-O-(trans-9"-Octadecenoyl)-5-ethynyl-1-β-D-ribofuranosyl-imidazole-4-carboxamide.

To a solution of 5-ethynyl-1-β-D-ribofuranosylimidazole-4-carboxamide (EICAR) (0.10 g, 0.37×10$^{-3}$ mol) in 5 ml anhydrous N,N-dimethylformamide and 5 ml pyridine was added 1 ml of a stock solution of trans-9-Octadecenoylchloride (0.13 g, 0.45×10$^{-3}$ mol) in 3 ml dichloromethane, and the reaction mixture was stirred under nitrogen at room temperature. The remaining stock solution was added in 1 ml portions at approx, 3 hours intervals. After a total of 50 hours reaction time, the solvents were evaporated at high vacuum, and the product was purified on a column of silica gel with 15% methanol in chloroform as the eluent system. Homogenous fractions were evaporated to give 30 mg (15%) of the title compound as a white solid.

$^1$H NMR (DMSO-$d_6$, 300 MHz) δ: 8.05(1H,s,H-2), 7.35 and 7.25(2H,s+s, $NH_2$), 5.65(1H,d,H-1'), 5.6(1H, br d, OH-2'), 5.35(3H,m,CH═CH and OH-3'), 4.91(1H,s, C≡CH), 4.3(1H,m,H-2'), 4.2(2H,m,H-5'), 4.05(2H,m,H-3' and H-4'), 2.30(2H,t,$CH_2$—COO), 1.95(4H,m,$CH_2$—C═), 1.45(2H,m,$CH_2$—C—COO), 1.25(20H,m,$CH_2$), 0.85(3H,t, $CH_3$).

$^{13}$C NMR (DMSO-$d_6$, 75 MHz) δ: 172.76(COO), 162.57 ($CONH_2$), 139.80(C-5), 135.82(C-2), 130.08(CH═CH), 115.51(C-4), 91.39(—C≡), 88.75(C-1'), 81.78(C-4'), 73.91 (C-2'), 71.46(≡CH), 70.09(C-3'), 63.57(C-5'), 33.66, 31.95, 31.29, 29.00, 28.84, 28.72, 28.55, 28.50, 28.42, 28.36, 24.49, 22.12($CH_2$), 13.97($CH_3$).

Following the procedure of examples 1–7, additional compounds of formula I can be prepared from the starting materials indicated, as follows:

TABLE 1

| | B—S—OH (1) | + | FaX (2) | → | B—S—O—Fa (3) | |
|---|---|---|---|---|---|---|
| Example No | Reactant (1) | | Reactant (2) | | Product (3) | |
| 8 | 2-β-D-ribofuranosyl-selenazole-4-carboxamide | | Oleic acid | | 2-(5'-O-oleyl-β-D-ribofuranosyl)-selenazole-4-carboxamide | |
| 9 | 4-hydroxy-3-β-D-ribofuranosyl-pyrazole-5-carboxamide | | Oleic acid | | 4-hydroxy-3-(5'-O-oleyl-β-D-ribo-furanosyl)-pyrazole-5-carboxamide | |
| 10 | 2'-deoxy-coformycin | | Elaidic acid | | 5'-O-elaidyl-2'-deoxy-coformycin | |
| 11 | 2'-deoxy-2'-fluoro-5-iodo-1-β-D-arabino-furanosyl-cytosine | | Elaidic acid | | 5'-O-elaidyl-2'-deoxy-2'-fluoro-5-iodo-1-β-D-aribino-furanosyl-cytosine | |
| 12 | (E)-5-(2-bromo-vinyl)-2'-deoxy-uridine | | cis-11-eicosenoic acid | | 5'-O-(cis-11-eicosenoyl)-(E)-5-(2-bromovinyl)-2'-deoxy-uridine | |
| 13 | 1-β-D-arabino-furanosyl-(E)-5-(2-bromovinyl)uracil | | Oleic acid | | 5'-O-(oleoyl)-1-β-D-arabinofuraosyl-(E)-5-(2-bromo-vinyl)uracil | |
| 14 | 9-(4-hydroxymethyl-2-cyclopentenyl)-guanine | | Oleic acid | | 9-(4-oleoylmethyl-2-cyclopentenyl)-guanine | |
| 15 | 2'-deoxy-2'-fluoro-1-β-D-arabino-furanosyl-1,2,4-triazole-3-carboxamide | | trans-11-eicosenoic acid | | 2'-deoxy-2'-fluoro-5'-O-(trans-11"-eicosenoyl)-1-β-D-arabinofuranosyl-1,2,4-triazole-3-carboxamide | |

It is noted that more products (3) can be obtained through all possible permutations by the reaction of the compounds referred to as reactant (1) with reactant (2). e.g. 5'-O-oleyl-2'-deoxy-coformycin, 5'-O- (cis-11"-eicosenoyl)-2'-dexoy-coformycin and 5'-O-(trans-11"-eicosenoyl)-2'-deoxy-coformycin.

We claim:

1. A monoester compound of formula I:

wherein O is oxygen, Nu is a nucleoside analogue, Fa is an acyl group of a mono-unsaturated C18 or C20 ω-9 fatty acid, which fatty acid is esterified with a hydroxyl group in the 5'-position of the sugar moiety of the nucleoside analogue or with a terminal hydroxyl group on the non-cyclic group of the nucleoside analogue, and wherein Nu is represented by the formula II:

B—S wherein S is either a mono-saccharide-derivative selected from: 1-β-D-ribofuranose, 1-β-D-arabinofuranose, 2-deoxy-1-β-D-ribofuranose, 2,3-dideoxy-1-β-D-ribofuranose, 2,3-didehydro-2,3-dideoxy-1-β-D-ribofuranose, 2-deoxy-2-fluoro-1-β-D-arabinofuranose, 2,2-dideoxy-3-azido-1-β-D-ribofuranose or 4-hydroxymethyl-2-cyclopenten-1-yl, or selected from the group of 2-hydroxy-ethoxy-methyl, 4-hydroxy-3-(hydroxymethyl-butyl, 2-hydroxyl-1-(hydroxymethyl)-ethoxy-methyl, 2,3-dihydroxy-propoxy or 2,3-dihydroxy-propyl; and B is a heterocyclic ring system selected from the following formulas:

(i)

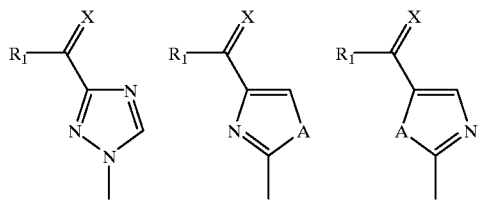

wherein X=O, S, NH and $R_1$=$NH_2$, $CH_3$, $CH_3O$ and A=NH, S, Se, $CH_2$, O, or (ii)

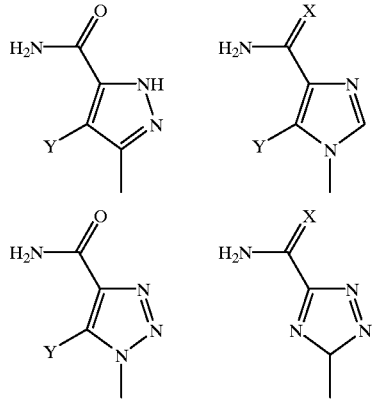

wherein X=NH, S, O and Y=H, OH, F, Cl, Br, I, $NH_2$, $CH_2CN$, C≡CH or (iii)

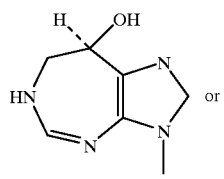

(iv)

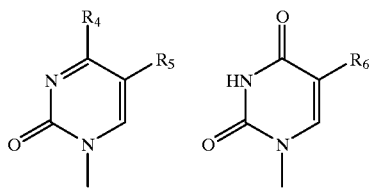

wherein $R_4$=H, $NH_2$, NHOH, $NHCOCH_3$, $NHCH_3$, $NHNH_2$ and $R_5$=H, F, Cl, Br, I, $CH_3$, $CF_3$ and $R_6$=$CH_3$, I, CH=CHBr, $CH_2OH$, $CH_2NH_2$, C≡$CCH_3$ or (v)

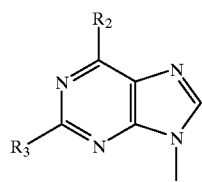

wherein $R_2$=OH, SH, H, Cl and $R_3$=H, OH, Cl, SH, $NH_2$; with the proviso that when S is 1-β-D-arabinofuranose, 2,3-dideoxy-3-azido-1-β-D-ribofuranose, 2-hydroxy-ethoxy-methyl, 4-hydroxy-3-(hydroxymethyl)-butyl, 2-hydroxy-1-(hydroxymethyl)-ethoxy-methyl or 2,3-dihydroxy-propoxy, then B cannot be (a)

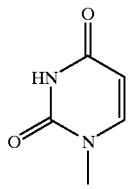

(b)

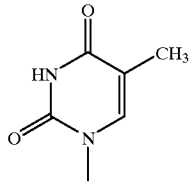

(c)

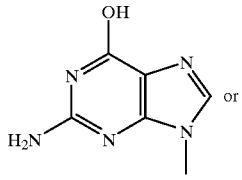

or (d)

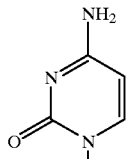

2. A compound according to claim 1, wherein Nu is ribavirin, selenazole, pyrazomycin, or 2'-deoxy-coformycin.

3. A compound according to claim 1, wherein Fa is oleic acid, elaidic acid, cis-eicosenic acid or trans-eicosenic acid.

4. A compound according to claim 1, wherein Nu is ribavirin and Fa is oleic acid.

5. A compound according to claim 1, wherein Nu is ribavirin and Fa is elaidic acid.

6. A compound according to claim 1, wherein Nu is ribavirin and Fa is cis-eicosenic acid or trans-eicosenic acid.

7. A pharmaceutical composition for the treatment of viral infections comprising a compound according to any one of claims 1 through 6 or 8 and a pharmaceutically acceptable carrier or excipient.

8. A compound according to claim 2 wherein Fa is oleic acid, elaidic acid, cis-eicosenic acid or trans-eicosenic acid.

9. A method of preparing a pharmaceutical composition for the treatment of a viral infection, comprising the steps of:
   (a) selecting a monoester compound according to claim 1 and
   (b) combining the monoester compound with a pharmaceutically acceptable carrier or excipient.

* * * * *

UNITED STATES PATENT AND TRADEMARK OFFICE
CERTIFICATE OF CORRECTION

PATENT NO. : 6,153,594
DATED : November 28, 2000
INVENTOR(S) : Bernt Børretzen et al.

It is certified that error appears in the above-identified patent and that said Letters Patent is hereby corrected as shown below:

Column 1,
Line 5, "Present" should read -- The present --.
Line 14, "anti viral" should read -- anti-viral --.
Line 41, "virus" should read -- viruses --.

Column 2,
Line 26, "symptom free" should read -- symptom-free --.
Line 55, "recurrencies" should read -- recurrences --.
Line 61, "long standing" should read -- longstanding --.

Column 3,
Line 50, "there have been" should be deleted.
Line 51, "developed" should be deleted.
Line 52, "the in particular" should read -- the nitrogen base or sugar moiety. In particular, --

Column 4,
Line 39, "The" should read -- the --.

Column 5,
Line 64, "$R_4=CH_3$" should read -- $R_6=CH_3$, --.

Column 7,
Line 56, "VII=FIAC," should read -- VIII=FIAC, --.

Column 9,
Line 23, "below.:" should read -- below: --.

Column 10,
Line 7, "mentioned," should read -- mentioned above, --.
Line 15, "Bovine 1,2,3,4," should read -- Bovine herpesvirus 1,2,3,4, --.
Lines 25, 33, 35 and 39, "administrered" should read -- administered --.
Line 62, "desired" should read -- desired, --.

Column 11,
Line 11, "anti viral" should read -- anti-viral --.
Line 26, "Plague" should read -- Plaque --.
Line 63, "lead" should read -- led --.

UNITED STATES PATENT AND TRADEMARK OFFICE
CERTIFICATE OF CORRECTION

PATENT NO.   : 6,153,594
DATED        : November 28, 2000
INVENTOR(S)  : Bernt Børretzen et al.

It is certified that error appears in the above-identified patent and that said Letters Patent is hereby corrected as shown below:

Column 12,
Line 11, "anti viral" should read -- anti-viral --.
Line 25, "an" should read -- a --.

Column 13,
Line 16, "$CH_2–CH_2$)." should read -- $CH_3–CH_2$). --.

Column 15,
Line 15, "$3.8 \times 10^{31\ 3} mol$)," should read -- $3.8 \times 10^{-3} mol$), --.
Line 29, "$CH_3–COO$)," should read -- $CH_2–COO$), --.
Line 46, "$CH_3–C$)" should read -- $CH_3–C$). --.
Line 63, "dichioromethane," should read -- dichloromethane, --.

Column 17,
Line 16, "(hydroxymethyl-butyl," should read -- (hydroxymethyl)-butyl, --.

Signed and Sealed this

Twenty-first Day of May, 2002

JAMES E. ROGAN
*Director of the United States Patent and Trademark Office*

*Attest:*

*Attesting Officer*